(12) United States Patent
Deane et al.

(10) Patent No.: US 7,730,887 B2
(45) Date of Patent: Jun. 8, 2010

(54) PORTABLE GAS FRACTIONALIZATION SYSTEM

(75) Inventors: Geoffrey Frank Deane, Goleta, CA (US); Brenton Alan Taylor, Santa Barbara, CA (US); Rex O. Bare, Lake Forest, CA (US); Andrew J. Scherer, Trabuco Canyon, CA (US); Bradley J. Sargent, Mission Viejo, CA (US); Andrew J. March, Lake Forest, CA (US); Joseph E. Merchant, Lake Forest, CA (US); Jeffrey C. Smith, Irvine, CA (US)

(73) Assignee: Inogen, Inc., Goleta, CA (US)

( * ) Notice: Subject to any disclaimer, the term of this patent is extended or adjusted under 35 U.S.C. 154(b) by 339 days.

(21) Appl. No.: 11/928,183

(22) Filed: Oct. 30, 2007

(65) Prior Publication Data

US 2008/0105258 A1 May 8, 2008

Related U.S. Application Data

(60) Division of application No. 10/962,194, filed on Oct. 7, 2004, now Pat. No. 7,438,745, which is a continuation-in-part of application No. 10/680,997, filed on Oct. 7, 2003, now Pat. No. 7,066,985, and a continuation-in-part of application No. 10/681,456, filed on Oct. 7, 2003, now Pat. No. 7,135,059, and a continuation-in-part of application No. 10/680,885, filed on Oct. 7, 2003, now abandoned, and a continuation-in-part of application No. 10/681,487, filed on Oct. 7, 2003, now abandoned.

(51) Int. Cl.
*A62B 7/00* (2006.01)
*H01M 2/02* (2006.01)

(52) U.S. Cl. .................. 128/205.12; 429/163; 429/176; 429/180

(58) Field of Classification Search ..................... 95/96; 128/205.12; 429/163, 176, 180
See application file for complete search history.

(56) References Cited

U.S. PATENT DOCUMENTS 2,195,565 A 4/1940 Fricke (Continued)

FOREIGN PATENT DOCUMENTS

EP 0 848 981 A1 6/1998

(Continued)

*Primary Examiner*—Robert A Hopkins
(74) *Attorney, Agent, or Firm*—Knobbe Martens Olson & Bear, LLP

(57) ABSTRACT

A portable gas fractionalization apparatus that provides oxygen rich air to patients is provided. The apparatus is compact, lightweight, and low-noise. The components are assembled in a housing that is divided into two compartments. One compartment is maintained at a lower temperature than the other compartment. The lower temperature compartment is configured for mounting components that can be damaged by heat. The higher temperature compartment is configured for mounting heat generating components. An air stream is directed to flow from an ambient air inlet to an air outlet constantly so that there is always a fresh source of cooling air. The apparatus utilizes a PSA unit to produce an oxygen enriched product. The PSA unit incorporates a novel single ended column design in which all flow paths and valves can be co-located on a single integrated manifold. The apparatus also can be used in conjunction with a satellite conserver and a mobility cart.

14 Claims, 28 Drawing Sheets

U.S. PATENT DOCUMENTS

| | | |
|---|---|---|
| 2,728,407 A | 12/1955 | Squier |
| 2,798,718 A | 7/1957 | Gross |
| 2,944,627 A | 7/1960 | Skarstrom |
| 3,258,899 A | 7/1966 | Coffin |
| 3,323,292 A | 6/1967 | Brown |
| 3,406,501 A | 10/1968 | Watkins |
| 3,703,068 A | 11/1972 | Wagner |
| 3,730,158 A | 5/1973 | St. Amand |
| 3,880,616 A | 4/1975 | Myers et al. |
| 3,922,149 A | 11/1975 | Ruder et al. |
| 3,976,050 A | 8/1976 | Glasser et al. |
| 4,054,133 A | 10/1977 | Meyers |
| 4,070,164 A | 1/1978 | Miwa et al. |
| 4,077,779 A | 3/1978 | Sircar et al. |
| 4,146,277 A | 3/1979 | Santoro |
| 4,222,750 A | 9/1980 | Gauthier et al. |
| 4,247,311 A | 1/1981 | Seibert et al. |
| 4,302,224 A | 11/1981 | McCombs et al. |
| 4,303,419 A | 12/1981 | Frank et al. |
| 4,342,573 A | 8/1982 | McCombs et al. |
| 4,371,384 A | 2/1983 | McCombs |
| 4,373,938 A | 2/1983 | McCombs |
| 4,378,982 A | 4/1983 | McCombs |
| 4,381,002 A | 4/1983 | Mon |
| 4,428,372 A | 1/1984 | Beysel et al. |
| 4,449,990 A | 5/1984 | Tedford, Jr. |
| 4,462,398 A | 7/1984 | Durkan et al. |
| 4,482,361 A | 11/1984 | Whysall |
| 4,491,459 A | 1/1985 | Pinkerton |
| 4,496,376 A | 1/1985 | Hradek |
| 4,502,873 A | 3/1985 | Mottram et al. |
| 4,509,959 A | 4/1985 | McCombs |
| 4,511,377 A | 4/1985 | McCombs |
| 4,516,424 A | 5/1985 | Rowland |
| 4,534,346 A | 8/1985 | Schlaechter |
| 4,545,790 A | 10/1985 | Miller et al. |
| 4,584,996 A | 4/1986 | Blum |
| 4,681,099 A | 7/1987 | Sato et al. |
| 4,686,974 A | 8/1987 | Sato et al. |
| 4,698,075 A | 10/1987 | Dechene |
| 4,706,664 A | 11/1987 | Snook et al. |
| 4,744,803 A | 5/1988 | Knaebel |
| 4,770,678 A | 9/1988 | Haslett, Jr. |
| 4,783,205 A | 11/1988 | Searle |
| 4,802,899 A | 2/1989 | Vrana et al. |
| 4,826,510 A | 5/1989 | McCombs |
| 4,877,429 A | 10/1989 | Hunter |
| 4,892,566 A | 1/1990 | Bansal et al. |
| 4,895,808 A | 1/1990 | Romer |
| 4,925,464 A | 5/1990 | Rabenau et al. |
| 4,971,609 A | 11/1990 | Pawlos |
| 5,002,591 A | 3/1991 | Stanford |
| 5,004,485 A | 4/1991 | Hamlin et al. |
| 5,005,570 A | 4/1991 | Perkins |
| 5,032,150 A | 7/1991 | Knaebel |
| 5,071,453 A | 12/1991 | Hradek et al. |
| 5,112,367 A | 5/1992 | Hill |
| 5,114,441 A | 5/1992 | Kanner et al. |
| 5,144,945 A | 9/1992 | Nishino et al. |
| 5,154,737 A | 10/1992 | Jenkins et al. |
| 5,226,933 A | 7/1993 | Knaebel et al. |
| 5,268,021 A | 12/1993 | Hill et al. |
| 5,275,642 A | 1/1994 | Bassine |
| 5,366,541 A | 11/1994 | Hill et al. |
| 5,427,609 A | 6/1995 | Zoglman et al. |
| 5,466,134 A | 11/1995 | Shaffer et al. |
| 5,474,595 A | 12/1995 | McCombs |
| 5,495,848 A | 3/1996 | Aylsworth et al. |
| 5,496,388 A | 3/1996 | Tellier |
| 5,531,807 A | 7/1996 | McCombs |
| 5,549,736 A | 8/1996 | Coffield et al. |
| 5,558,086 A | 9/1996 | Smith et al. |
| 5,578,115 A | 11/1996 | Cole |
| 5,593,478 A | 1/1997 | Hill et al. |
| 5,603,315 A | 2/1997 | Sasso, Jr. |
| 5,611,845 A | 3/1997 | Delp, II |
| 5,626,131 A | 5/1997 | Chua et al. |
| 5,630,411 A | 5/1997 | Holscher |
| 5,632,612 A | 5/1997 | Shaffer |
| 5,658,371 A | 8/1997 | Smolarek et al. |
| 5,665,316 A | 9/1997 | Salonia et al. |
| 5,697,364 A | 12/1997 | Chua et al. |
| 5,730,778 A | 3/1998 | Hill et al. |
| 5,735,268 A | 4/1998 | Chua et al. |
| 5,746,806 A | 5/1998 | Aylsworth et al. |
| 5,752,816 A | 5/1998 | Shaffer |
| 5,755,224 A | 5/1998 | Good et al. |
| 5,759,020 A | 6/1998 | Shaffer |
| 5,827,358 A | 10/1998 | Kulish et al. |
| 5,839,434 A | 11/1998 | Enterline |
| 5,865,174 A | 2/1999 | Kloeppel |
| 5,868,790 A * | 2/1999 | Vincent et al. ................. 607/5 |
| 5,871,564 A | 2/1999 | McCombs |
| 5,881,725 A | 3/1999 | Hoffman et al. |
| 5,890,490 A | 4/1999 | Aylsworth et al. |
| 5,906,672 A | 5/1999 | Michaels et al. |
| 5,912,426 A | 6/1999 | Smolarek et al. |
| 5,917,135 A | 6/1999 | Michaels et al. |
| 5,928,189 A | 7/1999 | Phillips et al. |
| 5,968,236 A | 10/1999 | Bassine |
| 5,979,440 A | 11/1999 | Honkonen et al. |
| 5,997,617 A | 12/1999 | Czabala et al. |
| 6,033,457 A | 3/2000 | Lawless |
| 6,036,754 A | 3/2000 | Rowe |
| 6,050,792 A | 4/2000 | Shaffer |
| 6,068,680 A | 5/2000 | Kulish et al. |
| 6,077,331 A | 6/2000 | Phillips |
| 6,129,530 A | 10/2000 | Shaffer |
| 6,146,447 A | 11/2000 | Sircar et al. |
| 6,152,134 A | 11/2000 | Webber et al. |
| 6,176,897 B1 | 1/2001 | Keefer |
| 6,178,772 B1 | 1/2001 | Incorvia |
| 6,186,142 B1 | 2/2001 | Schmidt et al. |
| 6,190,441 B1 | 2/2001 | Czabala et al. |
| 6,192,884 B1 | 2/2001 | Vann et al. |
| 6,220,244 B1 | 4/2001 | McLaughlin |
| 6,269,811 B1 | 8/2001 | Duff et al. |
| 6,299,670 B1 | 10/2001 | Applegarth |
| 6,311,719 B1 | 11/2001 | Hill et al. |
| 6,342,090 B1 | 1/2002 | Cao |
| 6,346,139 B1 | 2/2002 | Czabala |
| 6,348,082 B1 | 2/2002 | Murdoch et al. |
| 6,371,114 B1 | 4/2002 | Schmidt et al. |
| 6,372,026 B1 | 4/2002 | Takemasa et al. |
| 6,394,088 B1 | 5/2002 | Frye et al. |
| 6,395,065 B1 | 5/2002 | Murdoch et al. |
| 6,427,690 B1 | 8/2002 | McCombs et al. |
| 6,439,864 B1 | 8/2002 | Shaffer |
| 6,457,485 B2 | 10/2002 | Hill et al. |
| 6,478,850 B1 | 11/2002 | Warren |
| 6,497,755 B2 | 12/2002 | Murdoch et al. |
| 6,511,308 B2 | 1/2003 | Shaffer |
| 6,520,176 B1 | 2/2003 | Dubois et al. |
| 6,532,957 B2 | 3/2003 | Berthon-Jones |
| 6,532,958 B1 | 3/2003 | Buan et al. |
| 6,551,384 B1 | 4/2003 | Ackley et al. |
| 6,558,451 B2 | 5/2003 | McCombs |
| 6,581,297 B1 | 6/2003 | Ginder |
| 6,609,582 B1 | 8/2003 | Botti et al. |
| 6,629,525 B2 | 10/2003 | Hill et al. |
| 6,651,658 B1 | 11/2003 | Hill et al. |
| 6,712,877 B2 | 3/2004 | Cao et al. |
| 6,712,886 B2 | 3/2004 | Kim |
| 6,764,534 B2 | 7/2004 | McCombs |

| | | | | | | |
|---|---|---|---|---|---|---|
| 6,805,122 B2 | 10/2004 | Richey et al. | | 2004/0074496 A1 | 4/2004 | Hayashi et al. |
| 6,805,729 B2 | 10/2004 | Lim et al. | | 2004/0149133 A1 | 8/2004 | McCombs et al. |
| 6,811,590 B2 | 11/2004 | Lee et al. | | 2005/0072298 A1 | 4/2005 | Deane et al. |
| 6,848,444 B2 | 2/2005 | Smith et al. | | 2005/0072306 A1 | 4/2005 | Deane et al. |
| 6,866,041 B2 | 3/2005 | Hardy et al. | | 2005/0072423 A1 | 4/2005 | Deane et al. |
| 7,066,985 B2 | 6/2006 | Deane et al. | | 2005/0072426 A1 | 4/2005 | Deane et al. |
| 7,135,059 B2 | 11/2006 | Deane et al. | | 2005/0103341 A1 | 5/2005 | Deane et al. |
| 2002/0053286 A1 | 5/2002 | Czabala | | | | |
| 2002/0121191 A1 | 9/2002 | Warren | | | FOREIGN PATENT DOCUMENTS | |
| 2003/0005928 A1 | 1/2003 | Appel et al. | | | | |
| 2003/0024531 A1 | 2/2003 | Ball | | EP | 0988 882 A3 | 3/2000 |
| 2003/0167924 A1 | 9/2003 | McCombs et al. | | JP | 2002 231321 | 8/2002 |
| 2003/0192431 A1 | 10/2003 | Lee et al. | | WO | WO 01/41900 A2 | 6/2001 |
| 2004/0020366 A1 | 2/2004 | Walker et al. | | * cited by examiner | | |

PORTABLE GAS FRACTIONALIZATION SYSTEM

RELATED APPLICATIONS

This application is a divisional of U.S. patent application Ser. No. 10/962,194, filed Oct. 7, 2004, which is a continuation-in-part of U.S. patent application Ser. Nos. 10/680,997, 10/681,456, 10/680,885, and 10/681,487 all filed Oct. 7, 2003, which are hereby incorporated by reference in their entireties.

BACKGROUND OF THE INVENTION

1. Field of the Invention

This invention relates generally to a portable gas fractionalization system, more particularly, to a compact oxygen concentrator that is suitable for both in-home and ambulatory use so as to provide users greater ease of mobility.

2. Description of the Related Art

Patients who suffer from respiratory ailments such as Chronic Obstructive Pulmonary Diseases (COPD) often require prescribed doses of supplemental oxygen to increase the oxygen level in their blood. Supplemental oxygen is commonly supplied to the patients in metal cylinders containing compressed oxygen gas or liquid oxygen. Each cylinder contains only a finite amount of oxygen that typically lasts only a few hours. Thus, patients usually cannot leave home for any length of time unless they carry with them additional cylinders, which can be heavy and cumbersome. Patients who wish to travel often have to make arrangements with medical equipment providers to arrange for an exchange of cylinders at their destination or along the route, the inconvenience of which discourages many from taking extended trips away from home.

Supplemental oxygen can also be supplied by oxygen concentrators that produce oxygen concentrated air on a constant basis by filtering ambient air through a molecular sieve bed. While oxygen concentrators are effective at continual production of oxygen, they are typically large electrically powered, stationary units that generate high levels of noise, in the range of 50-55 db, which presents a constant source of noise pollution. Moreover, the units are too heavy to be easily transported for ambulatory use as they typically weigh between 35 to 55 lbs. Patients who use oxygen concentrators are thus tethered to the stationary machines and inhibited in their ability to lead an active life. While portable oxygen concentrators have been developed to provide patients with greater mobility, the currently commercially available portable concentrators do not necessarily provide patients with the ease of mobility that they desire. The portable concentrators tend to generate as much noise as the stationary units and thus cannot be used at places such as the theater or library where such noise is prohibited. Moreover, the present portable concentrators have very short battery life, typically less than one hour, and thus cannot be used continuously for any length of time without an external power source.

From the foregoing, it will be appreciated that there is a need for an apparatus and method that effectively provide supplemental oxygen to patients for both in-home and ambulatory use. To this end, there is a particular need for a portable oxygen concentrator that is lightweight, quiet, and can supply oxygen continuously for an extended period without requiring an external power source.

SUMMARY OF THE INVENTION

In one aspect, the preferred embodiments of the present invention provide a portable gas fractionalization apparatus comprising a PSA unit having plural adsorbent beds which produce oxygen having a purity of at least 87%; a compressor connected to supply compressed air to the PSA unit; and a blower which produces an air stream across the compressor. The PSA unit comprises valves operating in accordance with a PSA cycle that includes a pressure equalization step so as to provide greater than about 31% recovery of oxygen from air. Preferably, the valves of the PSA unit are disposed upstream of the air stream across the compressor such that thermal load on the PSA valves is reduced. Preferably, the compressor is a non-reciprocating compressor so as to reduce compressor noise, wherein the compressor is configured to draw ambient air at a flow rate of no more than about 15 slpm.

In one embodiment, the PSA unit comprises two adsorbent beds that operate in accordance with a six-step PSA cycle. Preferably, the PSA unit provides between about 31%-38% recovery of oxygen from air and produces an oxygen having a purity of between about 87%-93%. In another embodiment, the compressor comprises a scroll compressor configured to supply the compressed air to the PSA unit at a flow rate of between about 4 to 9 slpm and at a pressure of about 35 psia while generating a noise level of less than about 35 dB external to the compressor. In certain embodiments, the apparatus further comprises a heat exchanger which cools the compressed air to about the temperature of the ambient air prior to supplying the compressed air to the PSA unit. Moreover, the apparatus may also include a product gas delivery system which delivers oxygen to the patient at a flow rate of between about 0.15-0.75 slpm; a microprocessor control for recording data on apparatus performance or usage; and an infrared I/O port for transmitting the data to a remote location.

In another aspect, the preferred embodiments of the present invention provide a portable gas fractionalization apparatus comprising a housing having an air inlet and an air outlet wherein the housing is configured such that noise produced exterior to the fractionalization apparatus is no more than about 45 dB. The housing preferably contains components including a compressor, plural adsorbent beds, a battery having a rated life of at least 2 hours. The compressor is powered by the battery so as to draw air into the compressor preferably at a rate of about 15 slpm or less. Moreover, the housing and the components preferably have a combined weight of less than about 10 pounds.

In one embodiment, the apparatus further comprises a blower which is configured to draw ambient air through the air inlet to provide cooling for the components. Preferably, the housing comprises a circuitous air flow passageway for the ambient air to flow through, wherein the circuitous passageway extends between the air inlet and the air outlet and is configured to reduce noise due to air flow. In another embodiment, the compressor is preferably a scroll compressor configured to deliver a feed gas at a flow rate of between about 4 to 9 slpm and at a pressure of about 35 psia while generating a noise level of less than about 35 dB external to the compressor. In certain embodiments, the apparatus further comprises a plurality of sound baffles. Moreover, the housing may also comprise a vibration damper to reduce transfer of vibrational energy from the compressor to the housing.

In another aspect, the preferred embodiments of the present invention provide a method of producing an oxygen rich gas. The method comprises providing ambient air to a non-reciprocating compressor, wherein the ambient air is drawn into the compressor at a flow rate of less than about 15 slpm. The compressor pressurizes the ambient air and delivers the pressurized air to a PSA unit preferably at a flow rate of between about 4 to 9 slpm. The method further comprises processing the pressurized air in the PSA unit in accordance with a PSA cycle so as to produce an oxygen rich gas having a purity of between about 87%-93%. In one embodiment, the PSA cycle includes a pressure equalization step. In another embodiment, the PSA cycle is a six-step/two bed cycle. Preferably, the PSA unit operating in accordance with the PSA cycle provides greater than about 31% recovery of oxygen from the ambient air. In certain embodiments, the method further comprises generating an air stream across the compressor to provide cooling for the compressor.

In another aspect, the preferred embodiments of the present invention provide a portable gas fractionalization apparatus comprising plural adsorbent bed columns mounted side by side and an integral fluid flow manifold mounted on one end of the columns and comprised of a plurality of integrated flow passages and a plurality of valves which control flow of fluid through the integrated flow passages to and from the columns. In one embodiment, the apparatus further comprises a circuit board having circuitry which controls the valves. The manifold is preferably disposed between the circuit board and the one end of the columns. Preferably, contacts on the circuit board are in direct electrical contact with mating contacts on the valves. In one embodiment, the integrated fluid flow manifold comprises at least one piloted valve. In another embodiment, the integrated fluid flow manifold comprises at least one water trap positioned therein. The adsorbent columns preferably comprise one or more feed tubes configured to direct fluid to flow from flow passages in the integrated manifold mounted on one end of the columns to an opening in the other end of the columns. In one embodiment, the integrated manifold comprises an upper plate and a lower plate, each plate is made of a plastic material.

In another aspect, the preferred embodiments of the present invention provide a portable gas fractionalization apparatus comprising a compressor which produces a feed gas; plural adsorbent beds connected to receive the feed gas from the compressor via a feed gas pathway. The beds preferably provide a purified gas and a waste gas from the feed gas and the waste gas is expelled from the beds via a waste gas pathway. The apparatus further comprises a water trap which traps water condensed in the fluid pathway to prevent the water from reaching the beds. Preferably, the trapped water is located in the waste gas pathway such that the expelled waste gas carries the water away from the beds. In one embodiment, the water trap is positioned at a lower elevation relative to the feed gas pathway, wherein gravity causes the condensed water in the feed gas pathway to flow into the water trap located at the lower elevation. In another embodiment, the water trap is positioned in a laminated manifold, preferably in the center of a three way junction formed by airflow pathways to and from a feed valve, an exhaust valve, and a connection to an adsorbent bed.

In another aspect, the preferred embodiments of the present invention provide a portable gas fractionalization apparatus comprising a housing, a compressor mounted in the housing on a vibration damping member, and a compressor restraint connected between the compressor and the housing and sufficiently elastically yieldable to non-rigidly fasten the compressor to the housing. In one embodiment, the vibration damping member comprises a grommet having a plurality of ribs formed thereon. In another embodiment, the compressor restraint comprises an elastic tether having elongated legs configured with pre-formed bends which extend away from each other. The bends preferably can be pressed toward each other to straighten the legs and increase the overall length of the compressor restraint so as to facilitate mounting and removal of the compressor restraint.

In another aspect, the preferred embodiments of the present invention provide an adsorbent bed column comprising an elongated housing; an adsorbent material positioned inside the housing, and a first filter positioned proximate one end of the housing. The filter preferably comprises a generally annular member in sealing engagement with the housing, and a filter portion integrally formed as a single piece with the annular member. In one embodiment, the annular member comprises a silicone material and the filter portion comprises a woven fabric that is molded with the annular member. In another embodiment, the first filter is adapted to filter particulate greater than about 70 microns.

In another aspect, the preferred embodiments of the present invention provide an adsorbent bed column comprising an elongated housing; plural adsorbents positioned inside the housing; and a first filter comprised of a frit positioned proximate one end of the housing adjacent at least one adsorbent. In one embodiment, the column further comprises a second filter comprised of a frit positioned proximate the other end of the housing adjacent at least one adsorbent. Preferably, the first and second filters each has a thickness of at least 0.2 inch so as to be sufficiently thick to substantially restrain movement of the adsorbents inside the housing. In another embodiment, the column further comprises a wave spring positioned against an exterior surface of the first filter so as to apply a substantially even pressure over the first filter.

In another aspect, the preferred embodiments of the present invention provide a portable gas fractionalization apparatus comprising a compressor which compresses a gas, such as air, to provide a feed gas; plural adsorbent beds which receive said feed gas and output a purified gas and a waste gas; a battery which supplies power to said compressor; and a housing which comprises an ambient air inlet, an ambient air outlet, and plural compartments. Preferably, a first of the compartments contains the adsorbent beds and a second of the compartments contains the compressor, wherein the compartments significantly inhibit migration of thermal energy from the second compartment to the first compartment. In one embodiment, the apparatus further comprises an air circulation fan which draws air through the inlet into the first compartment, and through the first compartment into the second compartment, the air being exhausted through the outlet. Preferably, the fan is positioned directly above the compressor and produces an air stream directly against the compressor.

In one embodiment, the housing further comprises a circuitous air passageway having an upstream portion and a downstream portion through which the air is directed to flow. The upstream portion is preferably positioned adjacent the first compartment and the downstream portion is positioned adjacent the second compartment. Preferably, air in the downstream portion is substantially inhibited from flowing into the upstream portion. In one embodiment, the first compartment further contains heat sensitive components including a plurality of valves interconnected to the adsorbent beds and a circuit board having control circuitry which governs the operation of the valves. In another embodiment, the apparatus further comprises a plurality of sound absorbing baffles positioned along at least a portion of the air passageway.

In another aspect, the preferred embodiments of the present invention provide a portable gas fractionalization apparatus which includes a housing comprised of a chassis and a shell. The apparatus further includes a plurality of components mounted on and structurally supported by the chassis. Preferably, the shell covers the components and is removable from the chassis without removing the components. In one embodiment, the shell has a plurality of sidewalls, wherein at least one sidewall has a concave or convex section that provides curvature to the sidewall so as to reduce coupling of sound or vibration energy generated by components in the housing. In another embodiment, the shell has an opening adapted to receive a filter which filters fluid output from the apparatus wherein the filter is accessible from the exterior of the shell. Moreover, the chassis preferably comprises a plurality of integral structures adapted to receive and support the components, such as an integral compressor mount, an integral battery slot, and at least one integral gas flow passageway. Preferably, the chassis provides an intermediary vibration isolation between the components and the shell of the housing. In certain embodiments, the housing further includes a hatch that is removably attached to the shell to provide access to one or more components therein.

In another aspect, the preferred embodiments of the present invention provide a portable gas fractionalization apparatus comprising a compressor which produces a feed gas; plural adsorbent beds connected to receive the feed gas and produce a purified gas and a waste gas from the feed gas; a battery; and a conduit connected to deliver the waste gas to the battery to cool the battery. In one embodiment, the waste gas comprises a nitrogen rich gas. In another embodiment, the battery is positioned in a battery compartment such that the conduit delivers waste gas to a space between the battery and the battery compartment. Preferably, the battery compartment is comprised of a thermal sleeve positioned around the battery.

In another aspect, the preferred embodiments of the present invention provide a method of producing oxygen. The method comprises providing an oxygen concentrator having an air compressor which supplies compressed air to a PSA unit comprising plural adsorbent beds and a plurality of valves which control fluid flow to and from the beds; generating an air flow through the concentrator by inputting air through an inlet and outputting the air through an outlet, such that the air flows along a flow path through the concentrator; and exposing the valves to an upstream portion of the flow path and exposing the air compressor to a downstream portion of the flow path, such that the valves are substantially isolated from air that flows through the downstream portion of the flow path. Preferably, the air flow is generated using an air circulation fan to produce an air stream directly against the air compressor. In one embodiment, the method further comprises directing the air flow to flow along a circuitous flow path through the concentrator. Preferably, the air in the downstream portion of the flow path is substantially inhibited from circulating back into the upstream portion. In one embodiment, the method further comprises providing a plurality of sound baffles along at least a portion of the air flow path to reduce noise generated by the air flow and guide the air flow along the flow path.

In another aspect, the preferred embodiments of the present invention provide an apparatus for delivering oxygen to a patient. The apparatus comprises an oxygen concentrator having an oxygen delivery outlet, a flexible tube having a length of at least 10 feet, preferably between about 50 to 100 feet, one end of the tube connected to receive oxygen from the outlet, and a conserver which delivers oxygen in metered amounts in response to sensed breaths of the patient. The conserver is preferably connected to receive oxygen from the other end of the tube and delivers the oxygen to the patient. In one embodiment, the conserver comprises a breath sensor adapted to sense breaths of the patient and a delivery valve adapted for delivering oxygen to the patient. In another embodiment, the conserver further comprises an attachment member, preferably comprising a clip, adapted for removably attaching the conserver to the patient. In yet another embodiment, the conserver comprises a patient interface for setting oxygen flow rate. Preferably, the patient interface comprises an adjustment member such as a control knob which selects from a number of discrete flow rates and the adjustment member settings are read by a timing circuit that controls how long the value is open as a function of the adjustment member setting. In certain embodiments, the oxygen concentrator is a portable oxygen concentrator having a weight of no greater than about 10 pounds.

In another aspect, the preferred embodiments of the present invention provide a mobility cart for transporting a gas fractionalization unit. The mobility cart comprises a frame having a support portion and a handle portion, wherein the support portion is adapted to receive a portable gas fractionalization unit for transporting the unit in response to force on the handle portion. The mobility cart further comprises a power supply mounted on the frame, wherein the power supply has an A.C. power input, a first power outlet adapted to charge a battery, and a second power outlet adapted to power the unit. In one embodiment, the handle portion of the frame is configured with an extended position and a retracted position. Preferably, the height of the mobility cart is less than about 18 inches when the handle portion is in the retracted position. In another embodiment, the frame has a second support portion adapted to receive a battery. The second support portion may include a battery bail configured to mate with a plurality of guide rails formed on the battery in a manner so as to secure the battery to the battery bail. Preferably, the first power outlet is adapted to electrically interconnect to the battery when the battery is secured to the battery bail. Moreover, the first power outlet may be adapted to charge a spare battery or a battery mounted inside the unit. In certain embodiments, the power supply also has a third and a fourth power outlet, each adapted to charge a spare battery. Preferably, the power supply is sufficient to simultaneously power the unit and power the outlets for charging the spare batteries and the battery inside the unit.

In another aspect, the preferred embodiments of the present invention provide a wheeled mobility cart comprising a portable gas fractionalization unit; a frame to which the unit is removably connected for transporting the unit on the wheels; and a power supply mounted on the frame. Preferably, the power supply has an A.C. power input, a first power outlet adapted to charge a battery, and a second power outlet adapted to power the unit. Preferably, the portable gas fractionalization unit comprises an oxygen concentrator, more preferably an oxygen concentrator that weighs less than about 10 pounds. In one embodiment, the frame further comprises a handle portion configured with an extended position and a retracted position so as to facilitate storage of the cart.

In another aspect, the preferred embodiments of the present invention provide a battery pack for providing electrical power to a portable oxygen concentrator. The battery pack comprises a generally U-shaped body defined by a center portion and end portions. The center portion forms the bight of the U and the end portions form the legs of the U. The battery pack further comprises a top portion, a bottom portion, an exterior side portion and an interior side portion. The battery pack has a longitudinal axis that extends through the top and bottom portions and generally parallel to the side and end portions and passing through a wall of the interior side portion; a transverse axis that extends through the end portions and parallel to the side, bottom, and top portions and intersecting the longitudinal axis; a lower transverse axis that is parallel to the transverse axis and passes through the bottom portion and intersecting the longitudinal axis; a central lower lateral axis that is orthogonal to the longitudinal axis and intersecting both the longitudinal axis and the lower transverse axis; a first and second end lower lateral axes that are parallel to the central lower lateral axis and intersect the lower transverse axis and which pass through respective end portions. The battery pack further includes a contact protrusion extending from the bottom portion by about ⅜ inch or more. The contact protrusion has a first sidewall that is generally parallel to the lower transverse axis and has a length of about 1.5 inches or less. The contact protrusion also has a second sidewall that is generally parallel to the central lower lateral axis and has a length of about 0.5 inch or less. The distance between the exterior surfaces of the end portions measured along the lateral transverse axis is about 4.25 inches or less; the distance between the distance between the exterior surfaces of the side portions along the central lower lateral axis is about 1 inch or less; the distance between the exterior surfaces of the first end portion along the first end lateral lower axis is about 1.5 inches or less; and the distance between the exterior surfaces of the second end portion along the second end lateral lower axis is about 1.5 inches or less. Preferably, the battery pack is substantially symmetrical about the central lateral lower axis and asymmetrical about the lower lateral transverse axis. In one embodiment, the battery pack further comprises a handle portion extending upwardly from an upper surface of the body of the battery pack. The battery pack can also include at least one pair of guard rails or clips positioned on the interior side portion of the battery pack. Preferably, the distance between the guard rails is between about 1 and 1.5 inches and the guard rails are configure to engage with a battery bail. In one embodiment, the battery bail is mounted on the oxygen concentrator and/or mobility cart. In another embodiment, the battery pack further includes a casing and a plurality of battery cells enclosed therein, wherein at least a portion of the battery cells are arranged in a side-by-side array along a non-linear path.

In another aspect, the preferred embodiments of the present invention provide a battery pack for portable oxygen concentrators. The battery pack includes a plurality of battery cells; an asymmetrical housing having a U-shaped cross-section, wherein the housing encloses the battery cells therein and permits the battery cells to be positioned in a side-by-side arrangement along a non-linear path inside the housing; a handle portion extending from an upper surface of the housing; and a contact protrusion extends from a lower surface, preferably by ⅜ inch or more, of the housing for mating with power contacts on the concentrator. In one embodiment, the battery cells are selected from the group consisting of lithium ion cells, lithium polymer cells, nickel cadmium cells and nickel metal hydride cells. Preferably, the footprint of the battery pack has a length that is less than about 4.25 inches a width that is less than about 1.5 inches when the battery pack is mounted in an upright position in oxygen concentrator.

In another aspect, the preferred embodiments of the present invention provide an oxygen concentrator comprising at least one current actuated flow control valve, and a Pulse Width Modulated (PWM) current source connected to the at least one control valve by providing a PWM signal to the current source which converts the PWM signal to a valve actuation current. In one embodiment, a first current amplitude corresponding to a value of PWM duty cycle is sufficient to open or close the valve, and a second current amplitude which is lower than the first current amplitude and correspond to a lower PWM duty cycle is sufficient to maintain the valve in the open or closed state.

In another aspect, the preferred embodiments of the present invention provide an oxygen concentrator comprising a controller; at least one current actuated fan; and a Pulse Width Modulated (PWM) current source connected to the fan, wherein the controller actuates the fan by providing a PWM signal to the current source which converts the PWM signal to a fan actuation current.

In another aspect, the preferred embodiments of the present invention provide an oxygen concentrator comprising a controller; at least one current actuated compressor; a Pulse Width Modulated (PWM) current source connected to the compressor, wherein the controller actuates the compressor by providing a PWM signal to the current source which converts the PWM signal to a compressor actuation current. In one embodiment, the speed of the compressor varies with the amplitude of the compressor actuation current, wherein the compressor actuation current varies with the PWM duty cycle provided by the controller to the PWM current source. In another embodiment, the controller provides specific values of PWM duty cycle to the current source which correspond to selectable compressor speeds. In another embodiment, the controller provides specific values of PWM duty cycle to the current source which correspond to selectable compressor speeds. In another embodiment, the oxygen concentrator further comprises a compressor speed sensor, wherein the speed sensor is read by the controller which in turn adjusts the PWM duty cycle provided to the current source to vary the compressor actuation current so as to maintain desired compressor speed during periods when the load on the compressor varies.

DETAILED DESCRIPTION OF PREFERRED EMBODIMENTS

Figure 1:
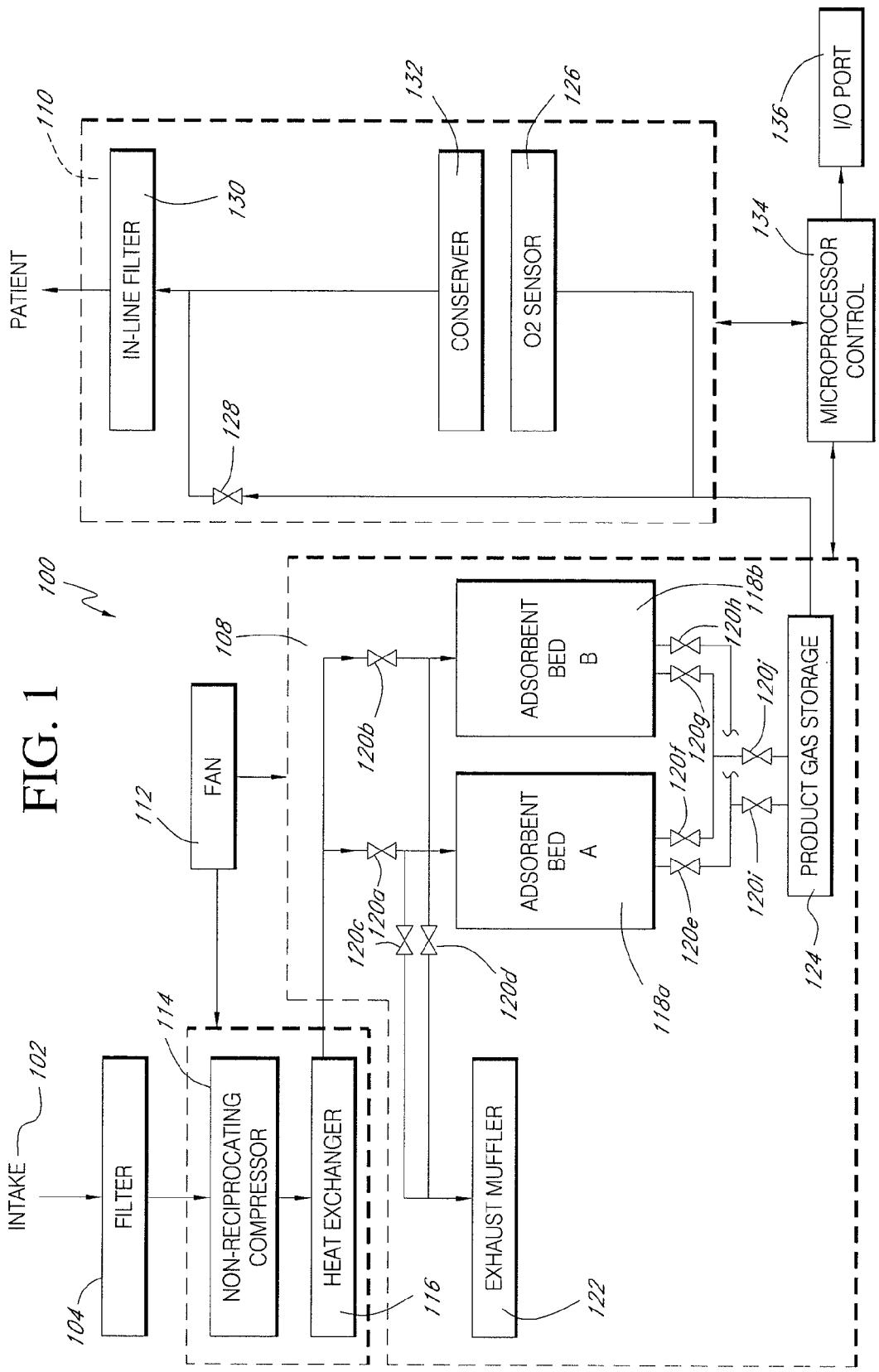
FIG. 1 is a block diagram of a portable gas fractionalization system of one preferred embodiment of the present invention.

FIG. 1 schematically illustrates a portable gas fractionalization system 100 of one preferred embodiment of the present invention. As shown in FIG. 1, the system 100 generally comprises an intake 102 through which ambient air is drawn into the system, a filter 104 for removing particulate from the intake air, a compressor assembly 106 for pressurizing the intake air to provide a feed gas, a pressure swing adsorption (PSA) unit 108 which receives and processes the feed gas to produce a product gas having a higher oxygen content than the ambient air, and a gas delivery system 110 for delivering the product gas to a patient.

Ambient air is drawn through the intake 102 at a relatively low flow rate, preferably no greater than about 15 standard liters per minute (slpm), so as to reduce noise due to airflow through the system. The system 100 further includes a fan 112 that produces an air stream across the compressor assembly 106 also preferably at a relatively low flow rate so as to provide cooling for the compressor assembly 106 without generating excessive noise.

As also shown in FIG. 1, the compressor assembly 106 includes a compressor 114 and an heat exchanger 116. The compressor 114 is preferably a non-reciprocating compressor, more preferably a scroll compressor described in U.S. Pat. Nos. 5,759,020 and 5,632,612, which are hereby incorporated by reference in their entirety. It is generally understood that a scroll compressor operates by moving a plate such that it orbits in a single plane relative to a fixed plate. Thus, the use of a scroll compressor advantageously eliminates reciprocating motion that tends to generate the excessive noise and vibration associated with many conventional piston compressors. In one embodiment, the scroll compressor 114 delivers an air flow of between about 4 to 9 slpm at a pressure of about 35 psia, while generating a noise level of less than about 35 dB external to the compressor. The scroll compressor 114 does not require lubricating oil and thus operates in a substantially oil-free environment, which advantageously reduces the likelihood of introducing oil contaminants into the compressed air. As FIG. 1 further shows, the compressor 114 works in conjunction with the heat exchanger 116 to provide cooled feed gas to the PSA unit 108. In one embodiment, the heat exchanger 116 has a large thermally conductive surface that is in direct contact with the air stream produced by the fan 112 such that pressurized air traveling through the heat exchanger 116 can be cooled to a temperature close to ambient prior to being supplied to the PSA unit 108.

The PSA unit 108 is configured to operate in accordance with a pressure swing adsorption (PSA) cycle to produce an oxygen enriched product gas from the feed gas. The general operating principles of PSA cycles are known and commonly used to selectively remove one or more components of a gas in various gas fractionalization devices such as oxygen concentrators. A typical PSA cycle entails cycling a valve system connected to at least two adsorbent beds such that a pressurized feed gas is sequentially directed into each adsorbent bed for selective adsorption of a component of the gas while waste gas from previous cycles is simultaneously purged from the adsorbent bed(s) that are not performing adsorption. Product gas with a higher concentration of the un-adsorbed component(s) is collected for use. Additional background information on PSA technology is described in U.S. Pat. No. 5,226,933, which is hereby incorporated by reference.

As shown in FIG. 1, the PSA unit 108 of a preferred embodiment includes two adsorbent beds 118a, 118b, each containing an adsorbent material that is selective toward nitrogen, and a plurality of valves 120a-j connected thereto for directing gas in and out of the beds 118a, 118b. As will be described in greater detail below, the valves 120a-j preferably operate in accordance with a novel PSA cycle which comprises a six step/two bed process that includes a pressure equalization step in which a portion of the effluent product gas from one bed is diverted to pressurize another bed in order to improve product recovery and reduce power consumption. One preferred embodiment of the PSA cycle comprises the following steps:

Step 1. Pressurize-Adsorbent Bed 118a/Production-Adsorbent Bed 118b pressurizing adsorbent bed 118a by directing feed gas into adsorbent bed 118a in the co-current direction at a feed pressure of about 35 psia while simultaneously diverting oxygen enriched product gas of higher pressure from adsorbent bed 118b into adsorbent bed 118a in the counter-current direction until pressures of the two beds 118a, 118b are substantially equalized;

releasing product gas from adsorbent bed 118b to a storage vessel 124 while stopping the flow of feed gas from entering adsorbent bed 118b;

Step 2: Feed-Adsorbent Bed 118a/Blowdown-Adsorbent Bed 118b feeding adsorbent bed 118a with feed gas at a rate of about 4-8.5 slpm at a feed pressure of about 35 psia;

counter-currently releasing nitrogen enriched waste gas from adsorbent bed 118b to an exhaust muffler 122;

Step 3: Feed and Production-Adsorbent Bed 118a/Purge-Adsorbent Bed 118b releasing product gas from adsorbent bed 118*a* to the storage vessel 124 while continuing to feed adsorbent bed 118*a* with feed gas at a rate of about 4-8.5 slpm. at a feed pressure of about 35 psia;

purging adsorbent bed 118*b* by releasing product gas from the storage vessel 124 to adsorbent bed 118*b* while continuing to counter-currently release waste gas from adsorbent bed 118*b* to the exhaust muffler 122;

Step 4: Production-Adsorbent Bed 118*a*/Pressurize-Adsorbent Bed 118*b* continuing to release product gas from adsorbent bed 118*a* to the storage vessel 124 while stopping the flow of feed gas from entering adsorbent bed 118*a*;

pressurizing adsorbent bed 118*b* by directing feed gas into adsorbent bed 118*b* in the co-current direction at a feed pressure of about 35 psia while simultaneously diverting product gas of higher pressure from adsorbent bed 118*a* into adsorbent bed 118*b* in the counter-current direction until pressures of the two beds 118*a*, 118*b* are substantially equalized;

Step 5: Blowdown-Adsorbent Bed 118*a*/Feed-Adsorbent Bed 118*b* counter-currently releasing waste gas from adsorbent bed 118*a* to the exhaust muffler 122;

feeding adsorbent bed 118*b* with feed gas at a rate of about 4-8.5 slpm at a feed pressure of about 35 psia;

Step 6. Purge-Adsorbent Bed 118*a*/Feed and Production-Adsorbent Bed 118*b* releasing product gas from adsorbent bed 118*b* to the storage vessel 124 while continuing to feed adsorbent bed 118*b* with feed gas at a rate of about 4-8.5 slpm at a feed pressure of about 35 psia;

purging adsorbent bed 118*a* by releasing product gas from the storage vessel 124 to adsorbent bed 118*a* while continuing to counter-currently release waste gas from adsorbent bed 118*a* to the exhaust muffler 122;

The PSA cycle described above advantageously includes one or more pressure equalization steps (steps 1 and 4) in which already pressurized product gas is released from one adsorbent bed to provide initial pressurization for another adsorbent bed until the two beds have reached substantially the same pressure. The pressure equalization step leads to increased product recovery and lower power consumption because it captures the expansion energy in the product gas and uses it to pressurize other adsorbent beds, which in turn reduces the amount of power and feed gas required to pressurize each bed. In one embodiment, the two-bed PSA unit shown in FIG. 1 operating in accordance with the above-described six-step/two-bed PSA cycle is capable of producing oxygen having a purity of at least about 87%, preferably between about 87%-93%, with greater than about 31% recovery of oxygen from feed gas, more preferably greater than about 38% recovery. In operation, the valves 120*a-j* of the PSA unit 108 are controlled in a known manner to open and close for predetermined time periods in accordance with the above described PSA steps. Additionally, the valves 120*a-j* are preferably positioned upstream of the air stream produced by the fan 112 across the compressor assembly 106 so as to not expose the valves 120*a-j* to portions of the air stream that are heated by the compressor assembly 106. In other embodiments, the system may utilize a vacuum swing adsorption (VSA) unit or a vacuum-pressure swing adsorption (VPSA) unit to produce the oxygen rich product gas.

As FIG. 1 further shows, the product gas produced by the PSA unit 108 is delivered to a patient via the product gas delivery system 110. The product gas delivery system 110 generally includes an oxygen sensor 126 for monitoring the oxygen content of the product gas exiting the storage vessel 124, a delivery valve 128 for metering the product gas to the patient, an in-line filter 130 for removing fine particulate in the product gas immediately prior to delivery to the patient, a conserver device 132 that controls the amount and frequency of product gas delivered based on the patient's breathing pattern. In certain embodiments, the product gas delivery system may also incorporate a unit that measures pressure within the storage vessel which in turn dictates the rate at which product gas is driven through the delivery valve. Preferably, product gas is delivered to the patient at a flow rate of about 0.15-0.75 slpm at about 90% oxygen content. In one embodiment, the system 100 also includes a microprocessor control 134 for collecting and recording data on system performance or patient usage pattern and an infrared port 136 for transmitting the data to a remote location.

Figure 2:
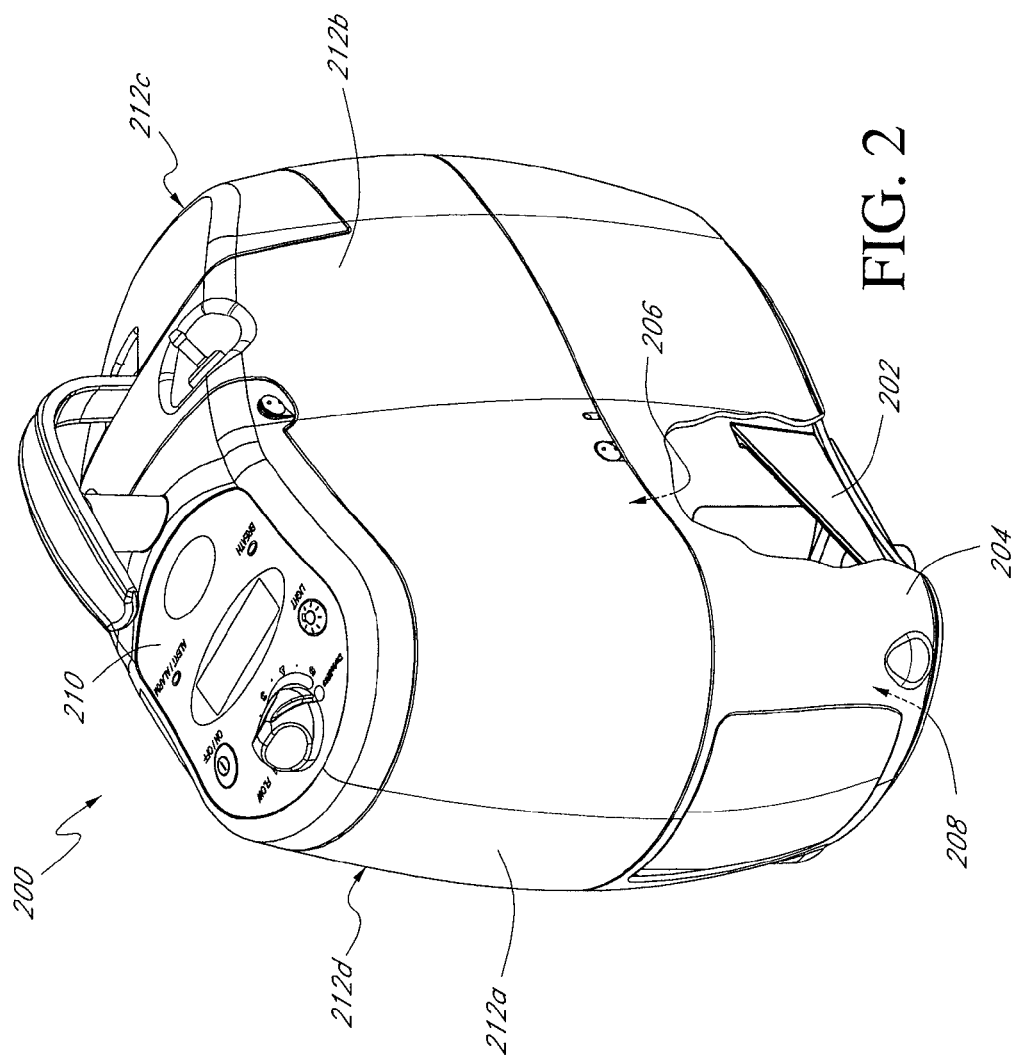
FIG. 2 is a perspective view of a portable gas fractionalization apparatus of another preferred embodiment, which is shown in the form of an oxygen concentrator.

FIG. 2 illustrates a gas fractionalization apparatus 200 of the preferred embodiment, which is shown in the form of a portable oxygen concentrator. As illustrated in FIG. 2, the apparatus 200 generally comprises a chassis 202 (see also FIG. 3) and a shell 204 that together form a housing 206 in which various components are mounted. The chassis 202 is removably attached to a base 208 of the housing 206. The base 208 has a substantially planar exterior bottom surface adapted to rest against a support surface such as a table or floor. The shell 204 of the housing 206 further includes an upper wall 210 and side walls 212*a-d*, each having at least one convex and/or concave section that provides a curvature to the wall so as to reduce coupling of sound or vibration energy generated by the components in the housing. Such curvature is also effective to reduce constructive interference of the coupled energy within the walls. Accordingly, the lack of planar sections in the walls 210, 212*a-d* of the housing 206 that are conducive to vibration reduces noise induced by vibration. Moreover, the non-planar walls 210, 212*a-d* also serve to discourage users from setting the housing on its side or placing it in any orientation other than the upright as the components inside the housing are designed to operate optimally in the upright orientation, which will be described in greater detail below.

Figure 3:
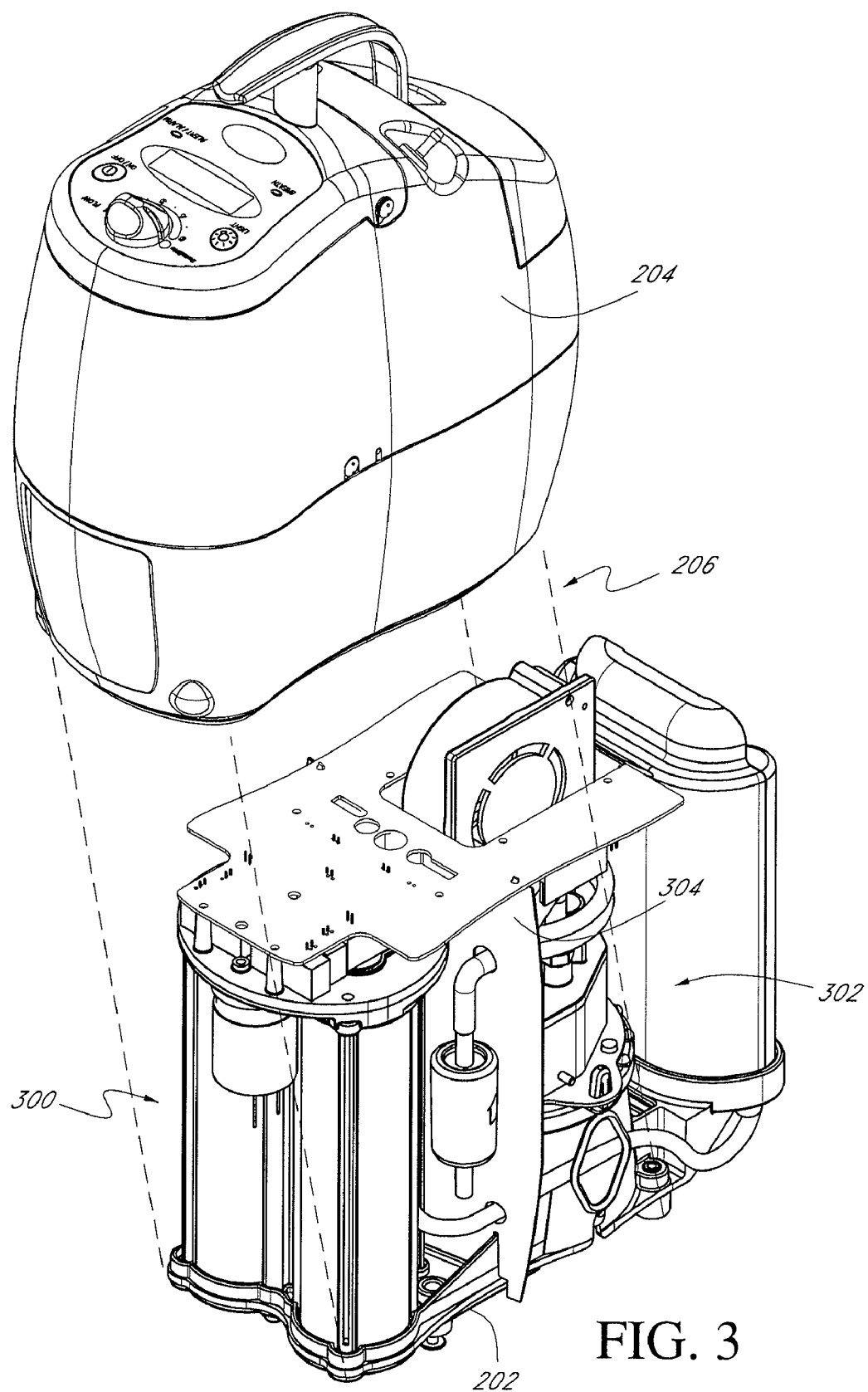
FIG. 3 is a perspective view of the apparatus of FIG. 2 as seen with the shell removed.

As shown in FIG. 3, the components in the housing 206 are structurally supported by the chassis 202 and the chassis 202 is removably attached to the shell 204. As such, the components can be assembled outside the confines of the shell 204. Also, the shell can be conveniently removed to provide access for testing, repair, or maintenance of the components. Additionally, the housing 206 is preferably separated into two compartments 300, 302 by a partition 304. The partition 304 in conjunction with an air flow system to be described in greater detail below significantly inhibits migration of thermal energy from the second compartment 302 to the first compartment 300. Preferably, heat sensitive components are placed in the first compartment 300 and heat generating components are mounted in the second compartment 302 so as to thermally isolate the heat sensitive components from the heat generating components for optimal system performance.

Figure 4:
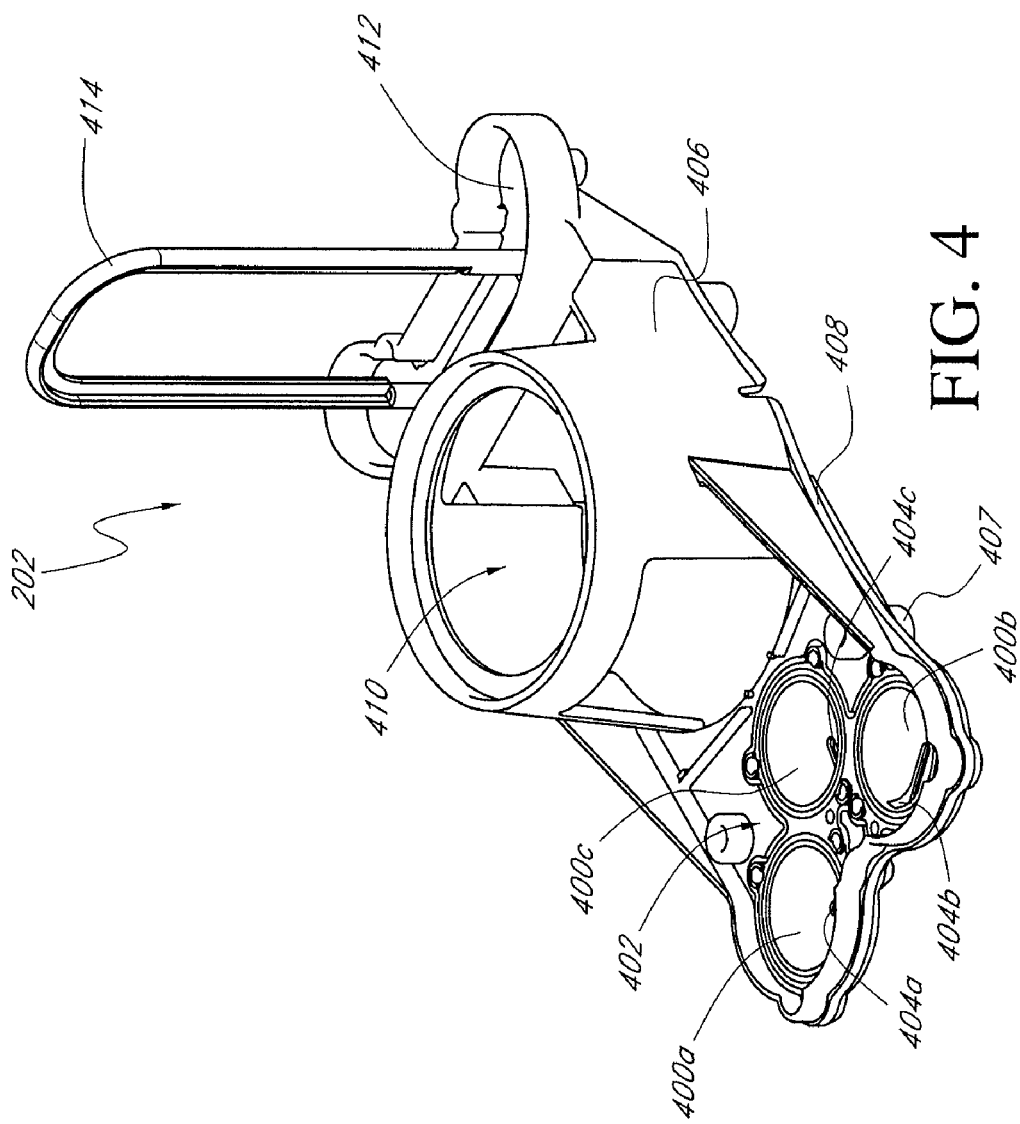
FIG. 4 is a perspective view of the chassis of the apparatus of FIG. 2.

FIG. 4 provides a detailed view of the chassis 202, as seen without the components. As shown in FIG. 4, the chassis 202 contains a number of pre-formed structures configured to receive and support the different components in the housing. Three circular recess 400*a-c* are formed in a first base portion 402 of the chassis 202 for mating with a PSA unit. Three corresponding divots 404*a-c* are also formed in the first base portion 402 immediately adjacent each respective recess 400*a-c*. The divots 404*a-c* extend laterally into each respective recess 400*a-c* to direct gas flow in and out of the PSA unit in a manner to be described in greater detail below. As such, the chassis serves as a manifold of sorts for routing gases to and from the PSA unit. An annular compressor mount 406 extends upwardly from a second base portion 408 of the chassis 202 to provide an elevated mounting surface for a compressor assembly and define an opening 410 sufficiently large to receive a portion of the assembly. As will be described in greater detail, the compressor mount 406 is configured to support the compressor assembly in a manner such that transfer of vibrational energy from the compressor assembly to the housing is reduced. As also shown in FIG. 4, an oblong slot 412 and a bail 414 are formed adjacent the compressor mount 406 for receiving and securing a battery. In one embodiment, electrical mating contacts are formed in the slot 412 for connecting the battery to operating circuitry. In one embodiment, a battery circuit is mounted on the bottom of the slot which can also contain a IRDA transmitter/receiver. Moreover, the chassis 202 can also be fit with notches to receive and support the bottom of the partition.

Preferably, at least some of the above-described structures of the chassis 202 are integrally formed via an injection molding process so as to ensure dimensional accuracy and reduce assembly time. These pre-formed structures in the chassis advantageously facilitate assembly of the components and help stabilize the components once they are assembled in the housing. In one embodiment, the chassis serves the function of providing an intermediary vibration isolation to the compressor and motor. As shown in FIG. 4, the chassis has bottom mounts or vibration isolation feet 407 that are configured to engage with the bottom of the shell. Preferably, screws are inserted through the bottom of the shell and into the bottom of the vibration feet 407. In another embodiment, the chassis further comprises an integrated muffler for exhaust gas. Preferably, a recess is formed below the battery slot in which felt or other porous material is placed. As will be described in greater detail below, an exhaust tube from the PSA unit is preferably ported directly into this recess and the felt serves to break up noise coming from the release of pressurized waste gas.

Figure 5:
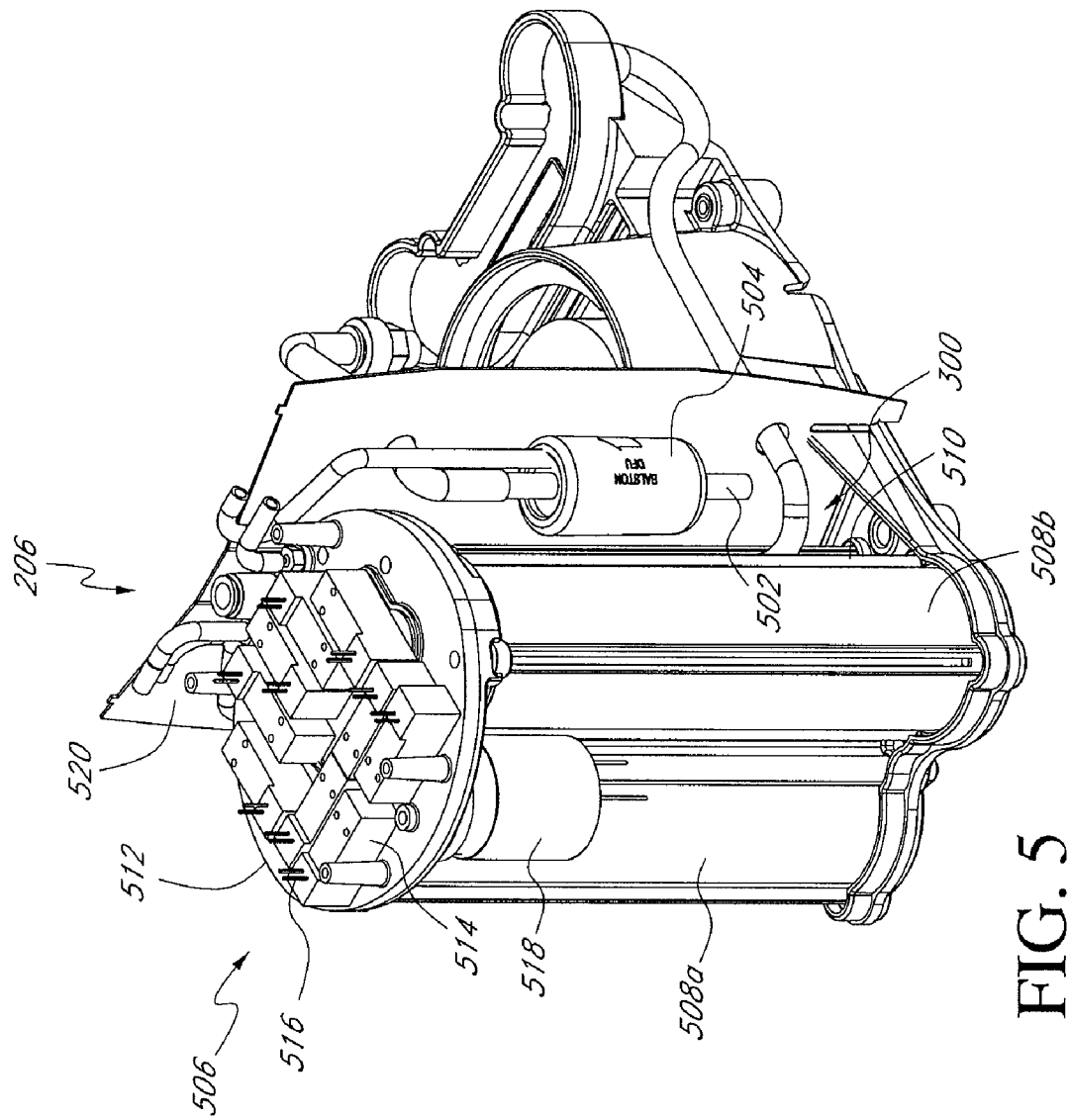
FIG. 5 is a perspective view of the components inside the first compartment of the apparatus of FIG. 2, showing a PSA unit.

FIG. 5 provides a detailed view of the components in the first compartment 300 of the housing 206. As shown in FIG. 5, the first compartment 300 generally contains an air intake 502, an intake filter 504, and a PSA unit 506. The air intake 502 is an elongated tube coupled to the intake filter 504 and extending downwardly therefrom to receive intake air. The intake filter 504 comprises a cylindrical shaped filter that is preferably capable of removing particles greater than about 0.1 microns from the intake air with about 93% efficiency. Moreover, the shape, density, and material of the intake filter 504 can be selected to provide the filter with acoustic properties so that the filter can also serve as an intake muffler. As will be described in greater detail below, the intake filter 504 is in fluid communication with a compressor system and supplies the compressor system with filtered intake air. Both the air intake 502 and the intake filter 504 are preferably mounted in the first compartment 300 of the housing 206 so as to avoid drawing higher temperature air produced by components in the second compartment into the system.

As FIG. 5 further shows, the PSA unit 506 generally includes a pair of adsorbent bed columns 508a, 508b, a product gas storage column 510, and an integrated manifold 512 for controlling fluid flow to and from the columns 508a-b, 510. Each adsorbent bed column 508a-b comprises an elongated housing containing a nitrogen-selective adsorbent material such as zeolite. The adsorbent bed columns 508a-b are adapted to remove nitrogen from intake air in a known manner in accordance with a PSA cycle so as to produce an oxygen rich product gas. The product gas storage column 510 comprises an elongated housing adapted to receive and store the oxygen rich product gas. In one embodiment, the product gas storage column 510 also contains an adsorbent material capable of holding a higher molar density of the product gas than an equivalent gas filled chamber at equal pressure. As shown in FIG. 5, all three columns 508a-b, 510 are mounted side by side in the housing 206. Preferably, the columns 508a-b, 510 have substantially the same length so that the integrated manifold 512 can be mounted horizontally on the upper end of the columns 508a-b, 510.

As will be described in greater detail below, the integrated manifold 512 contains a plurality of integrated flow passages formed in a single plane that permit fluid to flow to and from the columns 508a-b, 510. The integrated manifold 512 also has a plurality of solenoid valves 514 positioned in a single plane that control the flow of the fluid to and from the columns 508a-b, 510 during a PSA cycle. As shown in FIG. 5, the integrated manifold 512 is mounted on the upper end of the columns 508a-b, 510 in a manner such that the integrated flow passages in the manifold are in fluid communication with openings in the upper end of each column. While the manifold 512 is positioned on only the upper end of the columns, gas flow from the manifold can enter the column housing through either the upper or lower end due to a novel single-ended column design to be described in greater detail below. In one embodiment, the valves 514 of the manifold 512 contain a plurality of contact pins 516 adapted for direct contact with a circuit board in a manner to be shown in greater detail below. A circuit board controlling the valves can be mounted directly on top of the manifold 512 without additional wires, which advantageously simplifies the assembly process and also allows for the construction of a more compact device.

In one embodiment, an oxygen sensor 518 is mounted on the integrated manifold 512 and ported directly into a product gas flow passage in the manifold 512. The oxygen sensor 518 is configured to measure the oxygen concentration in the product gas using a galvanic cell or other known devices. Mounting the oxygen sensor 518 directly on the integrated manifold 512 results in a more compact assembly as it eliminates the use of tubing and connectors that are typically required to interconnect the oxygen sensor to the PSA unit. Moreover, it also places the oxygen sensor 518 closer to the product gas stream, which is likely to improve the accuracy and response time of the sensor. In another embodiment, a breath detector 520 is also ported into the integrated manifold 512. The breath detector 520 generally comprises one pressure transducer that senses pressure change in the product gas downstream of the product delivery valve (shown schematically in FIG. 1) caused by inhalation and exhalation of the patient so that the gas delivery frequency can be adjusted accordingly. The breath detector 520 may also include a second pressure transducer that senses the storage vessel pressure which is used to drive the delivery of the product to the patient through the product delivery valve. The breath detector 520 ports directly into the manifold instead of tapping into the product line downstream, which obviates the need of additional tubing connections and reduces the risk of leakage.

One of the key factors in creating a usable portable concentrator is long battery life. Battery life can be extended in several ways. For example, it can be extended by decreasing the power consumption of the concentrator while maintaining an acceptable performance level, and allowing for a wider range of battery voltage, such that the concentrator can continue to operate even after the battery voltage starts to decrease. Certain preferred embodiments of the present invention incorporate a Pulse Width Modulation (PWM) current control system to accomplish both lower power consumption and a wider range of battery voltage operation.

An oxygen concentrator typically includes flow control valves, such as solenoid type valves. Existing portable concentrators typically actuate the valves by applying a control voltage, which is at one level for ON (typically open valve) and another for OFF (typically closed valve). Such voltage controlled systems rely on well controlled voltage levels, with the ON level typically about 12 volts or more. However, in reality, many solenoid valves are actually actuated by current flow, and a high current is required to open the valve, but a much lower current is required to maintain the valve in the open position.

Figure 5A:
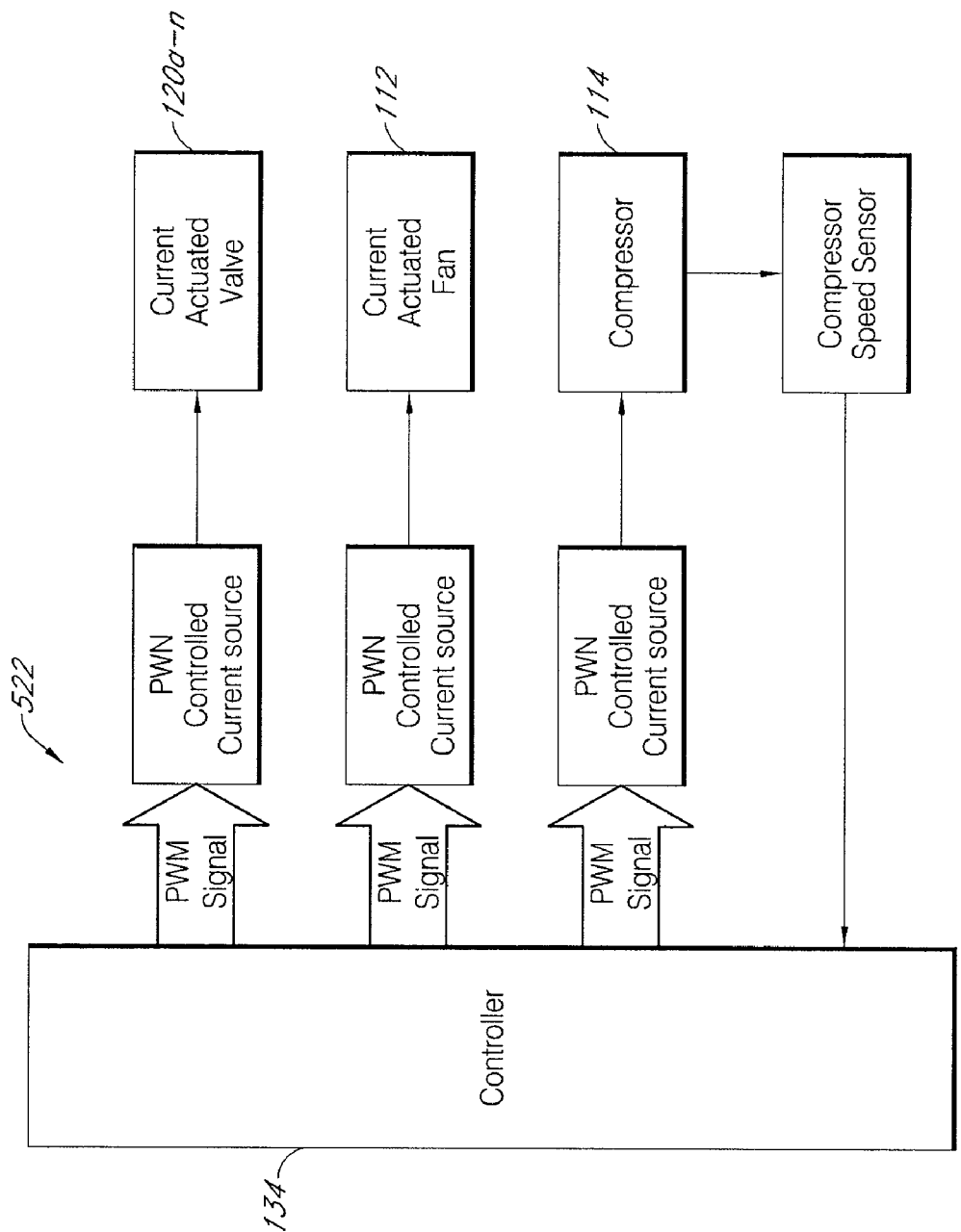
FIG. 5A is a schematic illustration of a Pulse Width Modulated (PWM) current source being used to control various components of the apparatus of FIG. 5.

Referring to FIG. 5A, the valves 120a-n are actuated by a two stage PWM controlled current source 522. In one embodiment, the controller 134 provides a digital control signal, preferably about 5 volts, a pulse train of variable duty cycle, which enables the current source. In the first stage, the current is controlled to a preset value for a preset time period so as to limit the voltage across the valve to a level which will be sufficient to guarantee rapid actuation while preventing excessive current. In the second stage, a preset current level maintains actuation of the valve while using minimum current. As is known in the art, varying the duty cycle essentially varies the amount of time the circuit is on, so PWM circuits can run on less power than always ON or OFF voltage controlled circuits, which allows for a much wider range of supply (battery) voltage. In addition, for valves 120a-n, the current required to actuate the valve corresponds to one value of the duty cycle, while the lower current to maintain actuation corresponds to a lower value of duty cycle. Thus the controller can achieve lower power consumption by reducing the duty cycle to the maintenance level to keep the valve open (or closed) once the valve is actuated. Valves which operate similarly, except ON corresponds to closed valve, are also contemplated by the invention.

The fan 112, typically used for cooling, may also be actuated with a PWM current source. The power draw of the fan circuit will be less with a PWM implementation. However the savings in power may not be worth the increased circuit complexity for all applications.

The compressor 114 may also be actuated with a PWM current source. In one embodiment, a speed sensor monitors the speed of the compressor. The flow rate of the concentrator is preferably determined by the speed of the compressor. In one embodiment, the concentrator has selectable flow rate settings which correspond to duty cycle settings for the PWM current source which powers the compressor. However, particularly when the concentrator is pressurizing, the load on the compressor is typically not constant. Therefore the controller can monitor the speed sensor and maintain the compressor speed substantially constant by adjusting the duty cycle controlling the current source to compensate for variation in the speed sensor output.

Advantageously, the PSA unit 506 has many novel features which, individually and in combination, contribute to a lighter, more compact and reliable apparatus. As shown in FIG. 5, the PSA unit 506 is mounted in the first compartment 300 which is thermally isolated from other heat generating components in the housing 206. Thermal isolation of the PSA unit 506 substantially prevents heat degradation of the valves 514 and other components in the unit. The PSA unit 506 is also configured with integrated gas flow passages so as to substantially eliminate the use of flexible tubing, which in turn reduces the number of potential leak points. Moreover, the PSA unit 506 is designed to operate with a single, generally planar integrated manifold mounted horizontally on one end of the columns. The single manifold design reduces the amount of space the PSA unit occupies inside the housing and also reduces potential leak points. Additionally, the PSA unit 506 is configured to directly connect to a circuit board without additional wires, which further conserves space and simplifies assembly.

Figure 6:
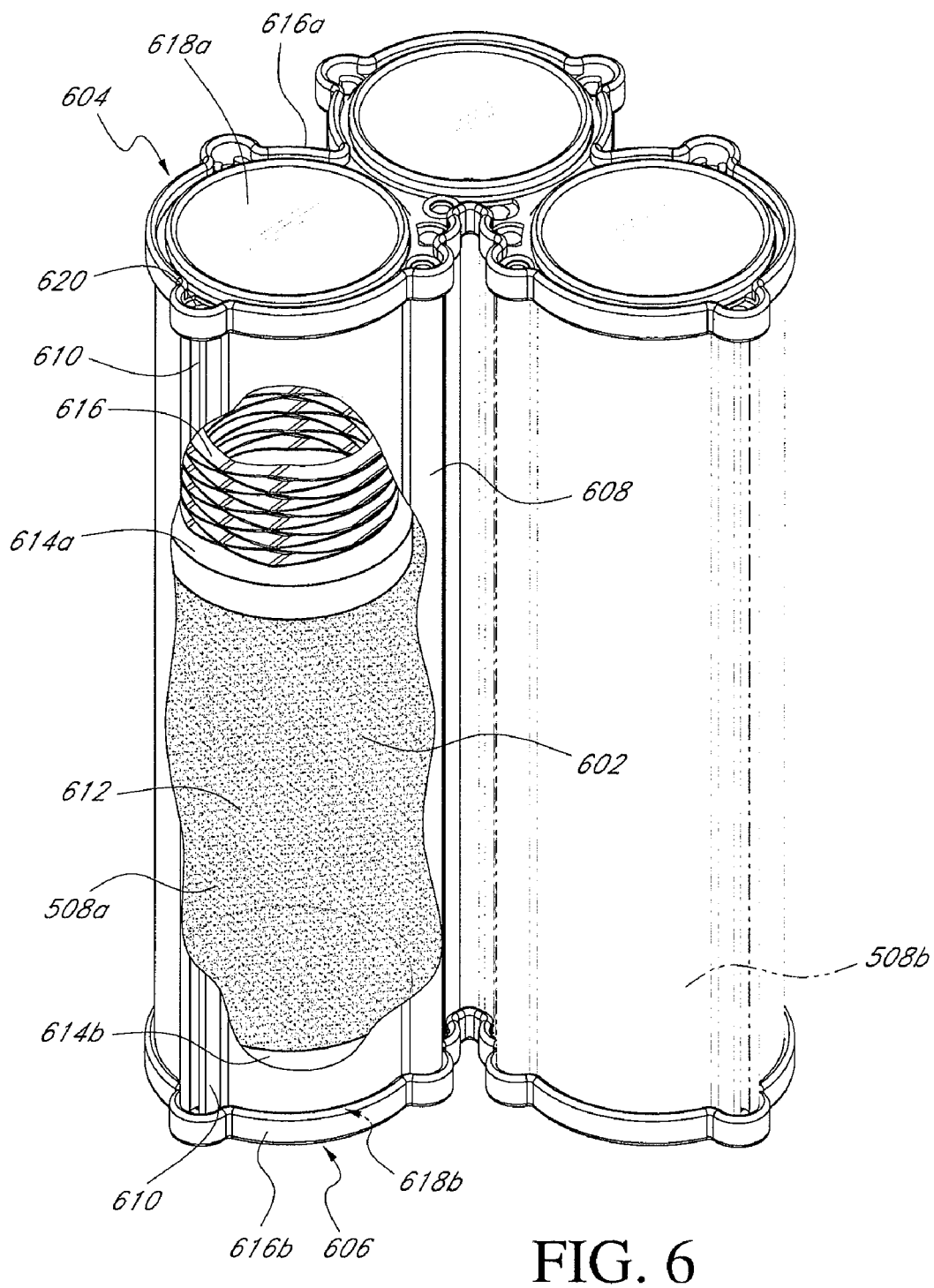
FIG. 6 is a schematic illustration of an adsorbent bed column of the PSA unit of FIG. 5.

FIG. 6 provides a detailed view of the adsorbent bed columns 508a, 508b of the PSA unit, illustrating the novel single-ended column design briefly described above. As shown in FIG. 6, the column 508a generally includes an elongated adsorbent housing 602 having an upper end 604 and a lower end 606, each defining an opening through which gas can flow in and out of the housing 602. The column 508a further includes an integrated feed tube 608 extending from the upper end 604 of the housing 602 to the lower end 606. The feed tube 608 provides a gas passageway between the manifold and the housing 602 such that gas from the manifold can be routed through the feed tube 608 into the lower end 606 of the housing 602 and vice versa. This design eliminates the need of a second manifold for directing gas into the lower end 606 of the housing 602 and allows all flow passages in the manifold to be co-located in a single plane, which significantly reduces the number of tubing connections and potential leak points in the unit.

The feed tube 608 preferably has a relatively small internal diameter to substantially minimize head space. It is generally recognized that the feed passage in a PSA unit represents head space, which is undesirable as it penalizes system performance. In one embodiment, the feed tube 608 has an internal diameter of about 0.125 inch and the adsorbent housing 602 has a diameter of about 1.5 inch. Moreover, the adsorbent housing 602 and the feed tube 608 are preferably integrally formed in an extrusion process so as to eliminate the use of flexible tubing and reduce potential leakage. In certain embodiments, the adsorbent bed column 508a further includes a plurality of threaded mounting members 610 positioned adjacent the adsorbent housing 602 for mating with screws that attach the column 508a to the chassis and manifold. The threaded mounting members 610 are preferably co-extruded with the housing 602 and the feed tube 608 so as to simplify part construction.

As also shown in FIG. 6, the adsorbent bed housing 602 contains an adsorbent material 612, an upper and a lower restraining disk 614a, 614b for inhibiting movement of the adsorbent material 612, a spring 616 that applies pressure across the upper restraining disk 614a to keep the disk 614a in position. In one embodiment, the adsorbent material 612 comprises a granular material such as zeolite that can be easily dislodged. The restraining disks 614a-b are preferably comprised of a frit material that can also serve as a filter for gross particulate, such as dislodged zeolite. Each restraining disk 614a-b has a diameter selected to form an interference fit with the internal walls of the housing 602 and has a thickness of at least about 0.2 inch, to provide some resistance to tilting of the disk, which may lead to leaks of particulate. The thickness of the disk 614a-b coupled with the nature of the frit material provide a tortuous path for particulate to travel through, which increases the effectiveness in trapping the particulate as compared to conventional paper filters. As also shown in FIG. 6, the upper restraining disk 614a is pressed against the adsorbent material 612 by the spring 616. The spring 616 is preferably a wave spring configured to apply substantially uniform pressure across the surface of the upper restraining disk 614a, so as to substantially inhibit the disk from tilting.

As also shown in FIG. 6, the adsorbent bed column 508a further includes annular gaskets 616a, 616b positioned adjacent to and in sealing engagement with the ends 604, 606 of the column 508a to contain the pressurized gases therein. In one embodiment, each annular gasket 616a-b further comprises an integrally formed filter portion 618a, 618b for filtering smaller particulate that cannot be captured by the restraining disks 614a-b. Preferably, the filter portion is capable of filtering particles greater than about 70-120 microns. In one embodiment, the gasket 616a-b is made of a silicone material and the filter portion 618a-b comprises a woven fabric, woven screen, or the like that is cast or molded together with the gasket. In another embodiment, the gasket 616a-b and filter portion 618a-b for all three columns of the PSA unit are injection molded as a single piece as shown in FIG. 6. Preferably, the filter portion 618a-b is embedded in the gasket 616a-b so as to facilitate placement of the filter portion and ensure a reliable seal between the gasket and the filter portion. Moreover, openings 620 are formed in each gasket 616a-b to accommodate openings in the feed tubes and the threaded mounting members.

Figure 7A:
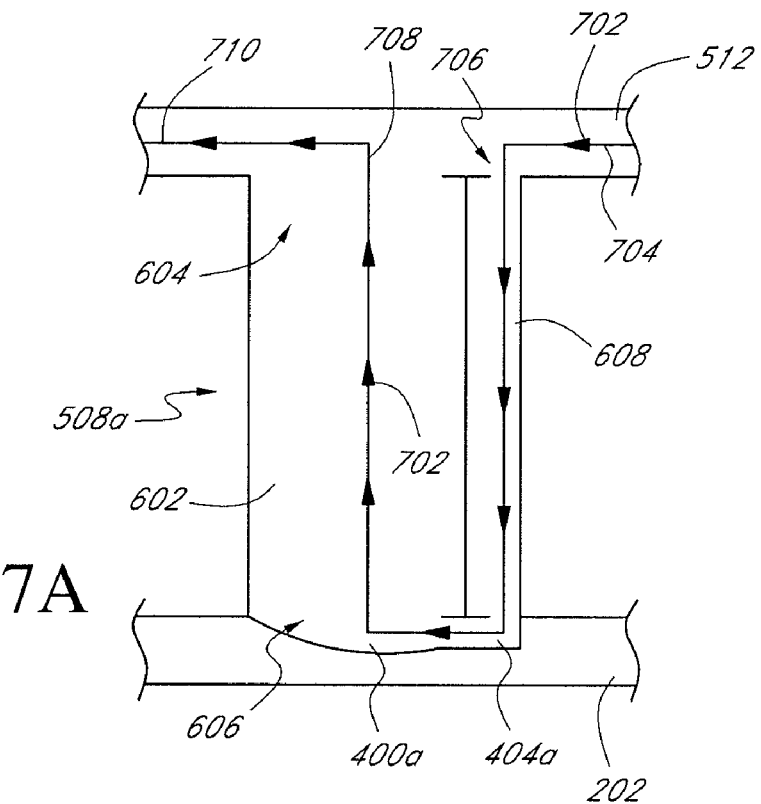
FIG. 7 is a schematic diagram of gas flow to and from the adsorbent bed column of FIG. 6.
Figure 7B:
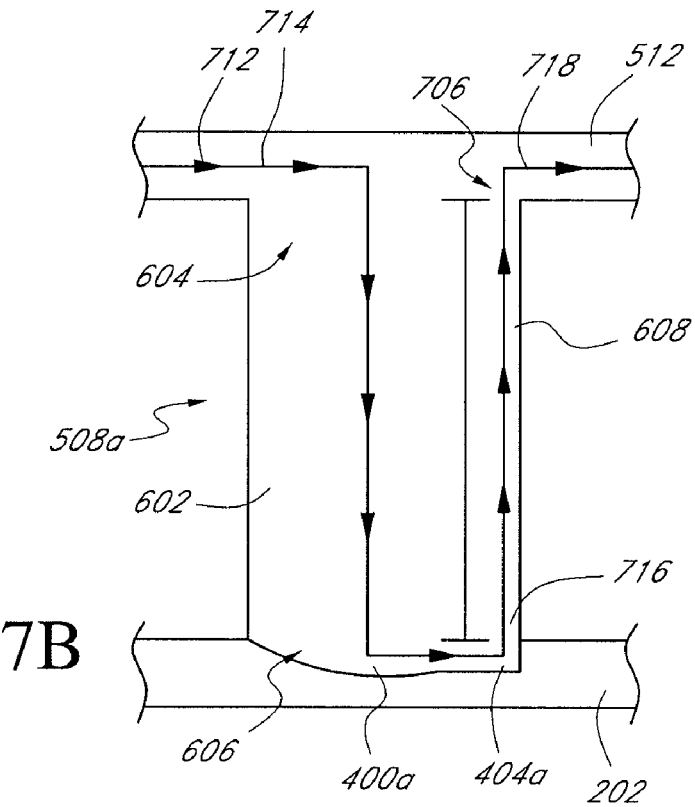

FIGS. 7A and 7B provide schematic illustrations of the adsorbent bed column 508a in combination with the chassis 202 and the manifold 512, showing the manners in which gas flow is directed in and out of the column 508a in accordance with the single-ended column design. As shown in FIG. 7A, feed gas 702 is directed from a feed stream 704 in the manifold 512 into an upper opening 706 of the feed tube 608. The feed gas 702 travels downwardly through the tube 608 and is diverted by a divot 404a in the chassis 202 into a recess 400a underneath the lower end 606 of the adsorbent housing 602. The divot 404a, which is pre-formed in the chassis 202, advantageously serves as a lateral gas flow passageway so as to eliminate the need of any flexible tubing on the lower end of the column, which in turn simplifies assembly and reduces potential leak points. The feed gas 702 flows upwardly from the recess 400a through the lower end 606 of the housing 602 and upwardly through the adsorbent material contained in the housing 602. The adsorbent material selectively removes one or more components in the feed gas 702 in a known manner to form a product gas 708. The product gas 708 flows out of an upper end 604 of the housing 602 into a product stream 710 in the manifold 512. FIG. 7B shows the manner in which purge gas is directed in and out of the column. As shown in FIG. 7B, purge gas 712 from a product stream 714 in the manifold 512 is directed through the upper end 604 of the housing 602 downwardly into the housing 602 to flush out the gas therein. The purge gas 712 exits the lower end 606 of the housing 602 and is channeled through the divot 404a. The divot 404a directs the purge gas 712 to flow into a lower opening 716 of the feed tube 608. The purge gas 712 exits the feed tube 608 through its upper opening 706 and enters a waste stream 718 in the manifold 512. As FIGS. 7A and 7B illustrate, the single-ended column design in conjunction with the divot formed in the chassis allow gas from a single-planed manifold to enter and exit the adsorbent housing through either the upper or lower end of the housing.

Figure 8:
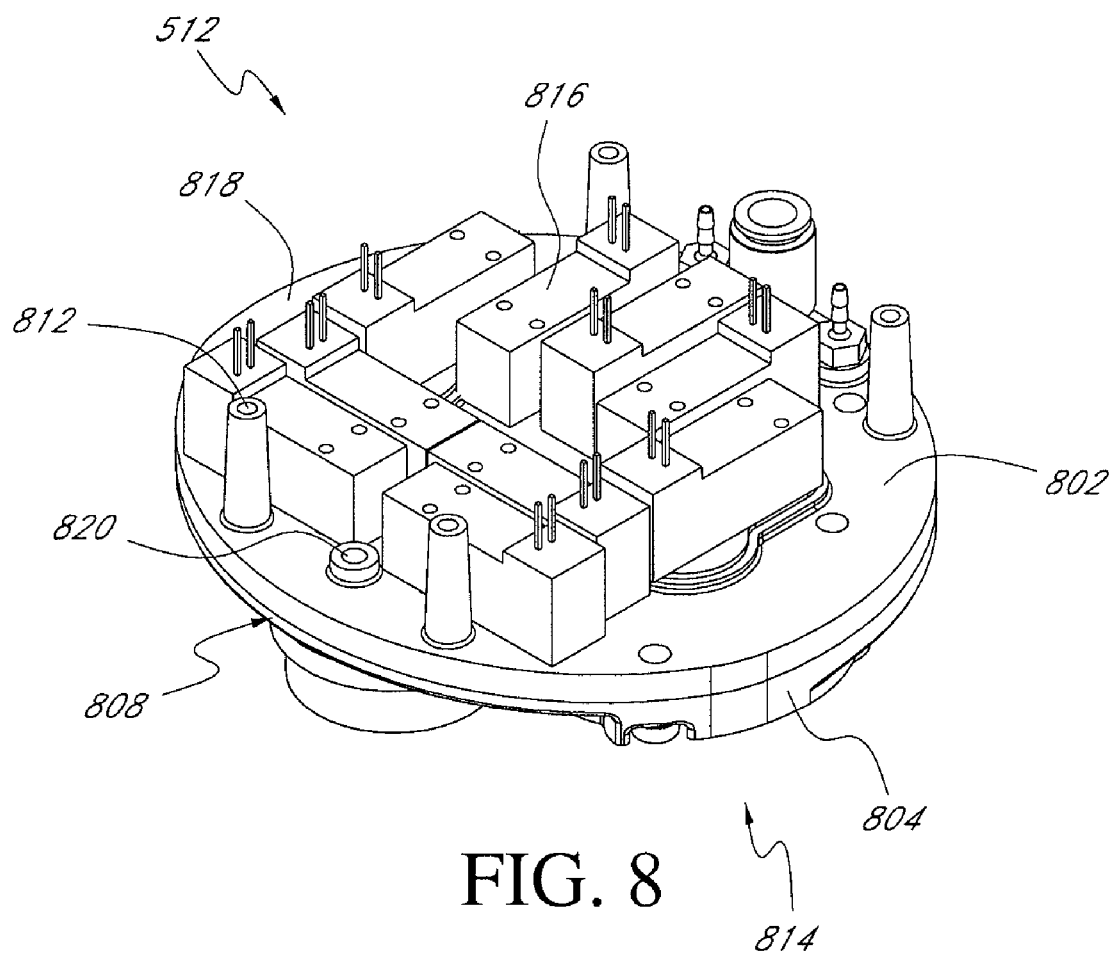
FIG. 8 is a detailed view of the integrated manifold of the PSA unit of FIG. 5.

FIG. 8 provides a detailed view of the integrated manifold 512 of the PSA unit. As shown in FIG. 8, the integrated manifold 512 generally includes an upper plate 802 and a lower plate 804, each having grooves formed in an inner surface thereof. The grooves of the lower plate align with those of the upper plate so as to form fluid passages in the manifold 512 when the upper plate 802 is affixed to the lower plate 804. The fluid passages may include feed gas pathways, waste gas pathways, and gas pathways interconnecting the adsorbent columns. The specific pattern of the fluid passages in the manifold can vary, depending on the particular application, although the passages of the preferred embodiment correspond to the circuit of FIG. 1. As also shown in FIG. 8, the upper plate 802 has a feed gas inlet 812 through which pressurized air from the compressor system is directed into the manifold 512. The lower plate 804 has a waste gas outlet 814 through which exhaust gas is expelled from the manifold 512 and a plurality of openings to connect the fluid passages with the adsorbent columns. Solenoid valves 816 are mounted on an upper surface 818 of the upper plate 802 in a known manner to control the flow of fluid between the fluid passages and the PSA columns. Bores 820 are also formed in the upper and lower plates 802, 804 for receiving fasteners used to mount the plates together and onto the PSA columns. In one embodiment, the plates 802, 804 of the manifold 512 are made of a plastic material formed by injection molding and laminated together via an adhesive bond applied in a vacuum. When compared to conventional laminated manifolds that are typically constructed of machined metal plates, the integrated manifold 512 formed by injection molding is advantageously lighter and less costly to manufacture.

Figure 9:
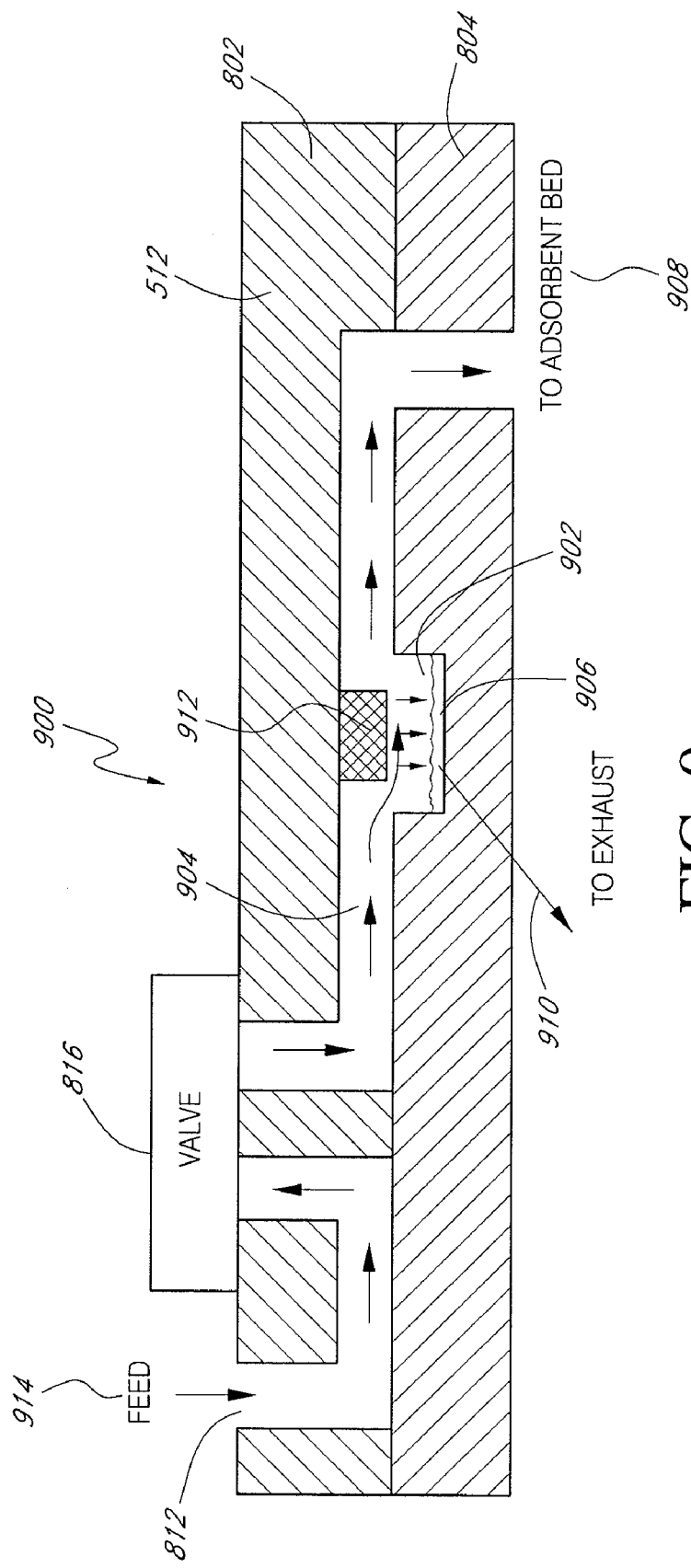
FIG. 9 is a schematic illustration of a water trap system incorporated in the integrated manifold of FIG. 8.

FIG. 9 schematically illustrates a water trap system 900 integrated in the manifold 512 for removing moisture from the feed gas prior to delivery to the columns. As shown in FIG. 9, the water trap system 900 generally includes an integrated water trap 902 formed in the manifold 512 and in fluid communication with a feed gas pathway 904. The water trap 902 is adapted to trap condensed water 906 in the feed gas by gravity so as to prevent the water from reaching the adsorbent bed 908. Preferably, the water trap 902 is located in a waste gas pathway 910 such that expelled waste gas carries the condensed water out through the exhaust.

In one embodiment, the water trap 902 is configured as a recess in the lower plate 804 of the manifold 512, extending downwardly from a section of the feed gas pathway 904 located in the upper plate 802. The water trap 902 is positioned at a lower elevation relative to the feed gas pathway 904 so as to substantially prevent trapped water 908 from re-entering the feed gas pathway 904. In certain embodiments, a baffle 912 is positioned in the feed gas pathway 904 to divert the feed gas flow downwardly into the water trap 902 so that the gas is required to rise upwardly to return to the feed gas pathway 904, which substantially prevents any condensed water from being carried past the water trap by the feed gas flow. As also shown in FIG. 9, the water trap 902 is in line with the waste gas pathway 910 located in the lower plate 804 of the manifold 504 so that the water trap 902 can be purged by waste gas flowing through the pathway 910. In one embodiment, the water trap 902 is located in center of a three way junction formed by the airflow passages to and from the feed valve, the exhaust valve, and the connection to the top of the column.

In operation, feed gas 914 enters the manifold 512 through the feed gas inlet 812 in the upper plate 802 and is directed through a solenoid valve 816 into the feed gas pathway 904. The feed gas 914 flows across the recessed water trap 902 such that condensed water 906 in the feed gas 914 settles into the water trap 902 by gravity while the lighter components continue along the pathway 904 into the adsorbent bed 908. Preferably, the water trap 902 containing the condensed water 906 is subsequently purged by gas in the waste gas pathway 910. It will be appreciated that the integrated water trap system is not limited to the above-described embodiment. Any integrated water trap system that encompasses the general concept of forming an integrated gas flow path having a lower region where light air flows past and moisture air condenses due to gravity are contemplated to be within the scope of the invention.

Figure 10:
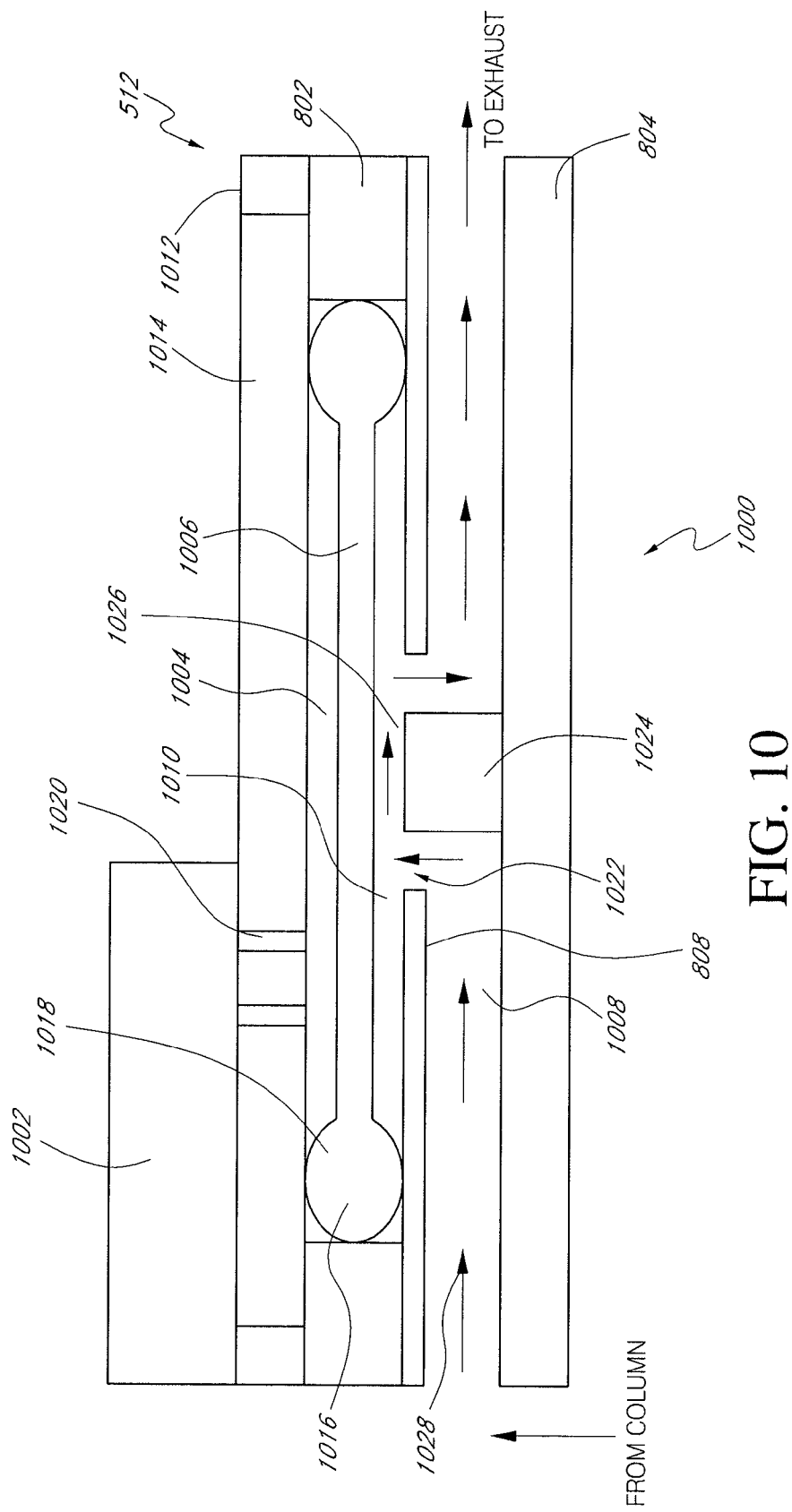
FIG. 10 is a schematic illustration of a piloted valve system incorporated in the integrated manifold of FIG. 8.

FIG. 10 schematically illustrates a piloted valve system 1000 integrated in the manifold 512 for providing quick release of pressurized gas from the adsorbent columns during a PSA cycle. It is generally recognized that the efficiency of a PSA cycle benefits from fast release of the pressurized gas within the adsorbent columns during the blow down and purge steps. However, the solenoid valves controlling gas flow from the columns to the waste gas pathway are typically limited in orifice size which in turn results in restricted flow and slowed release of the gas within the columns. To increase the flow capacity, the piloted valve system 1000 shown in FIG. 10 utilizes a solenoid valve to drive a much larger piloted valve that is embedded in the manifold and controls the waste gas flow to and from the columns.

As shown in FIG. 10, the piloted valve system 1000 generally includes a solenoid valve 1002, an air chamber 1004 in fluid communication with the solenoid valve 1002, and a piloted valve 1006 that can be actuated by the solenoid valve 1002 through the air chamber 1004. The piloted valve 1006 preferably comprises a diaphragm 1006 positioned between the air chamber 1004 and a waste gas pathway 1008. Pressure differences between the air chamber 1004 and the waste gas pathway 1008 mechanically deflect the diaphragm 1006 to open or close the waste gas pathway 1008 to gas flow. Preferably, the diaphragm 1006 has a natural resiliency such that it is deflected away from the waste gas pathway 1008 when the air chamber 1004 is not pressurized.

In one embodiment, the diaphragm 1006 is seated in a recess 1010 that extends downwardly from an exterior surface 1012 of the upper plate 802. An insert 1014 is mounted in the recess 1010 above the diaphragm 1006 and flush with the exterior surface 1012 of the plate 802. The diaphragm 1006 has an outer rim 1016 that sealingly engages with an inner surface 1018 of the insert 1014 so as to form the air chamber 1004 as shown in FIG. 10. The insert 1014 contains a plurality of openings 1020 that are in fluid communication with the air chamber 1004. The solenoid valve 1002 is mounted above the insert 1014 and controls gas flow through the openings 1020 to the air chamber 1004.

As also shown in FIG. 10, the waste gas pathway 1008 is formed in the lower plate 804 of the manifold and in contact with the diaphragm 1006 through an opening 1022 formed in the inner face 808 of the upper plate 802. To close the waste gas pathway 1008 from gas flow, the diaphragm 1006 is deflected toward a baffle 1024 positioned in the waste gas pathway 1008 and sealingly engages with the baffle 1024 so as to block off a pathway 1026 between the diaphragm and the baffle. To open the waste gas pathway 1008, the diaphragm 1006 is deflected away from the baffle 1024 so as to allow gas to flow through the pathway 1026 and out the exhaust. It will be appreciated that the pathway 1026 controlled by the diaphragm 1006 provides a much large flow capacity for waste gas than the orifices in the solenoid valves.

In operation, pressurized purge gas 1028 from the adsorbent column flows into the opening 1022 in the upper plate 802 and pushes the diaphragm 1006 away from the baffle 1024 so as to open the path 1026 between the diaphragm 1006 and the baffle 1024 for gas flow. After the purge gas is released through the exhaust, a portion of the feed gas is directed into the air chamber 1004 via the solenoid valve 1002 to push the diaphragm against the baffle 1024 so as to close the path 1026 therebetween. Advantageously, the piloted valve system 100 allows waste gas to be released from the column through a much larger opening than the orifices contained in the solenoid valves and does not consume additional space as the valves are all incorporated in the manifold.

Figure 11:
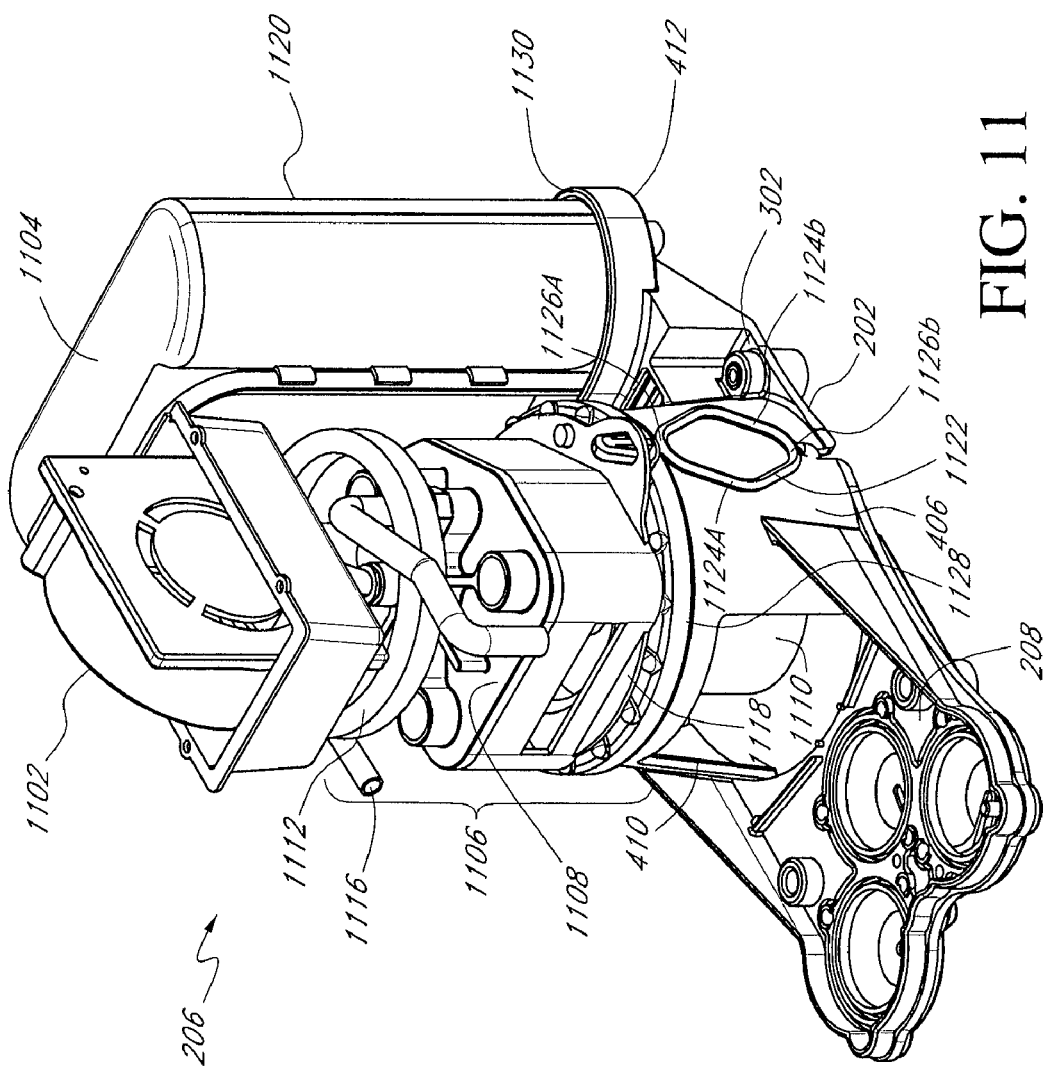
FIG. 11 is a perspective view of the components inside the second compartment of the apparatus of FIG. 2, showing a compressor system.

FIG. 11 provides a detailed view of the components inside the second compartment 302 of the housing 206. As shown in FIG. 11, the second compartment 302 generally contains an air circulation fan 1102, a battery 1104, and a compressor assembly 1106. In one embodiment, the fan 1102 comprises a blower or other device used for forcing air circulation. The battery 1104 is preferably a lithium ion battery having a rated life of at least 2 hours. In certain embodiments, the battery may also comprise a fuel cell or other transportable electric power storage device. The compressor assembly 1106 includes a compressor 1108, a driving motor 1110, and a heat exchanger 1112. In one embodiment, the compressor 1108 is preferably a non-reciprocating compressor such as a scroll compressor or a radial compressor and the motor 1110 is preferably a DC brushless motor. In certain embodiments, the compressor 1108 can also be a vacuum pump or a combination of a vacuum pump and a compressor. The heat exchanger 1112 can be in the form of aluminum coiled tubes or other common heat exchanger designs. In one embodiment, the heat exchanger 1112 has an inlet 1114 and an outlet 1116. The inlet 1114 is in fluid communication with the compressor 1108 for receiving feed gas therefrom and the outlet 1116 is connected to the PSA unit for delivery feed gas thereto.

As also shown in FIG. 11, the compressor 1108 rests on an upper surface 1118 of the compressor mount 406, which is elevated above the base 208 of the housing. The driving motor 1110 attached to the compressor 1108 extends into the opening 410 in the compressor mount 406 and remains suspended therein. Moreover, the heat exchanger 1112 is positioned above the compressor 1108 and under the fan 1102. Preferably, the fan 1102 directs an air flow against the heat exchanger 1112 to facilitate cooling of the feed gas therein. As also shown in FIG. 11, the battery 1104 is mounted on the battery bail 414 via three pairs of guide rails 1120 formed on the battery and adapted to mate with the battery bail 414. The distance between the guide rails 1120 becomes progressively shorter from bottom to top, with the topmost pair forming the tightest fit with the bail 414. This facilitates mounting of the battery particularly for those with impaired dexterity. When the battery 1104 is in position, the topmost guide rails are held firmly by the bail 414 while a lower section 1130 of the battery 1104 is held firmly by the mated electrical connectors formed in the battery slot 412.

In one embodiment, a compressor restraint 1122 is connected between the compressor 1108 and the chassis 202 to secure the compressor 1108 to the housing 206. Preferably, the compressor restraint 1122 comprises an elastic tether that fastens the compressor 1108 to the chassis. Preferably, the chassis is fit with grooves for engaging with the compressor restraint. In one embodiment, the compressor restraint 1122 comprises two elongated legs 1124a, 1124b spaced apart in the middle and joined together in an upper end 1126a and a lower end 1126b. The upper end 1126a is removably attached to the compressor 1108 and the lower end 1126b removably attached to the chassis 202. Moreover, the elongated legs 1124a, 1124b preferably have preformed bends which extend away from each other. These bends can be pressed toward each other to straighten the legs and increase the overall length of the compressor restraint 1122 so as to facilitate mounting and removal of the compressor restraint. Preferably, the compressor restraint does not substantially exert active force on the compressor assembly when the housing is in its upright position so as to reduce vibration coupling from the compressor to the chassis.

Figure 12:
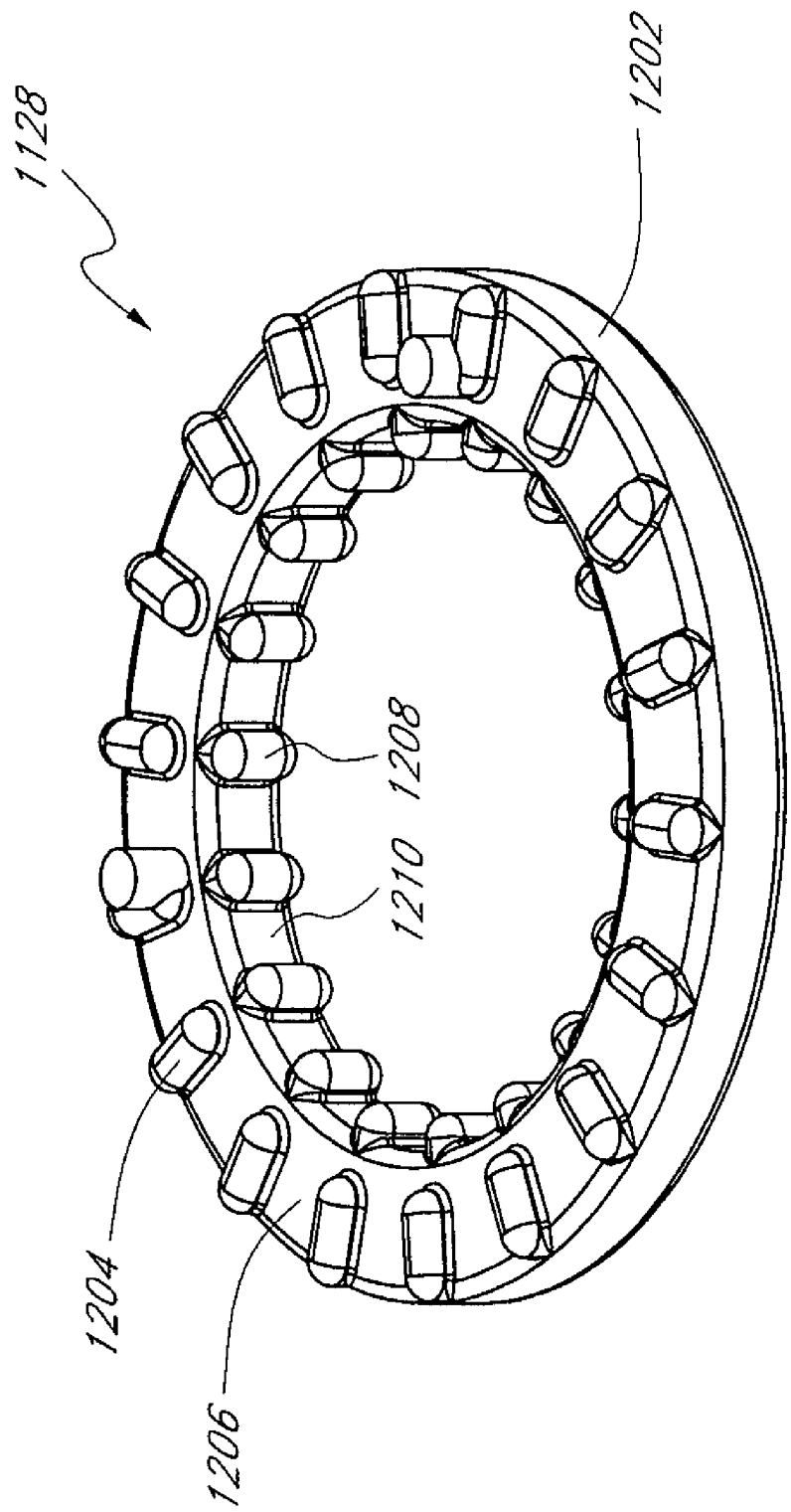
FIG. 12 is a perspective view of a vibration damping member incorporated in the compressor system of FIG. 11.

In another embodiment, a vibration damping member 1128 is interposed between the compressor mount 406 and the compressor 1108 to further reduce transfer of vibrational energy from the compressor to the housing. As shown in FIG. 12, the vibration damping member 1128 comprises a grommet 1202 configured to mate with the annular compressor mount so as to provide a vibration damping mounting surface for the compressor system. Preferably, the grommet 1202 is made of a resilient silicone material such as sorbothane and configured to absorb low vibrational frequencies produced by the compressor. In one embodiment, a first set of ribs 1204 are formed along the periphery of an upper surface 1206 of the grommet 1202 and configured to absorb vibration from the compressor. In another embodiment, a second plurality of ribs 1208 are formed on an inner surface 1210 of the grommet 1202 and configured to absorb vibration from the motor. The ribs 1204, 1208 substantially reduce the amount of vibration transferred to the grommet 1202 which is in contact with the compressor mount. The compressor advantageously rests on the grommet without being pressed against the chassis during normal operations and is restrained by the compressor restraint only when the apparatus is tipped over on its side. The vibration damping member 1128 is advantageously configured to reduce transfer of vibration energy, particularly low frequency vibration, from the compressor system to the housing, thus reducing noise created by vibration of the housing.

Figure 13:
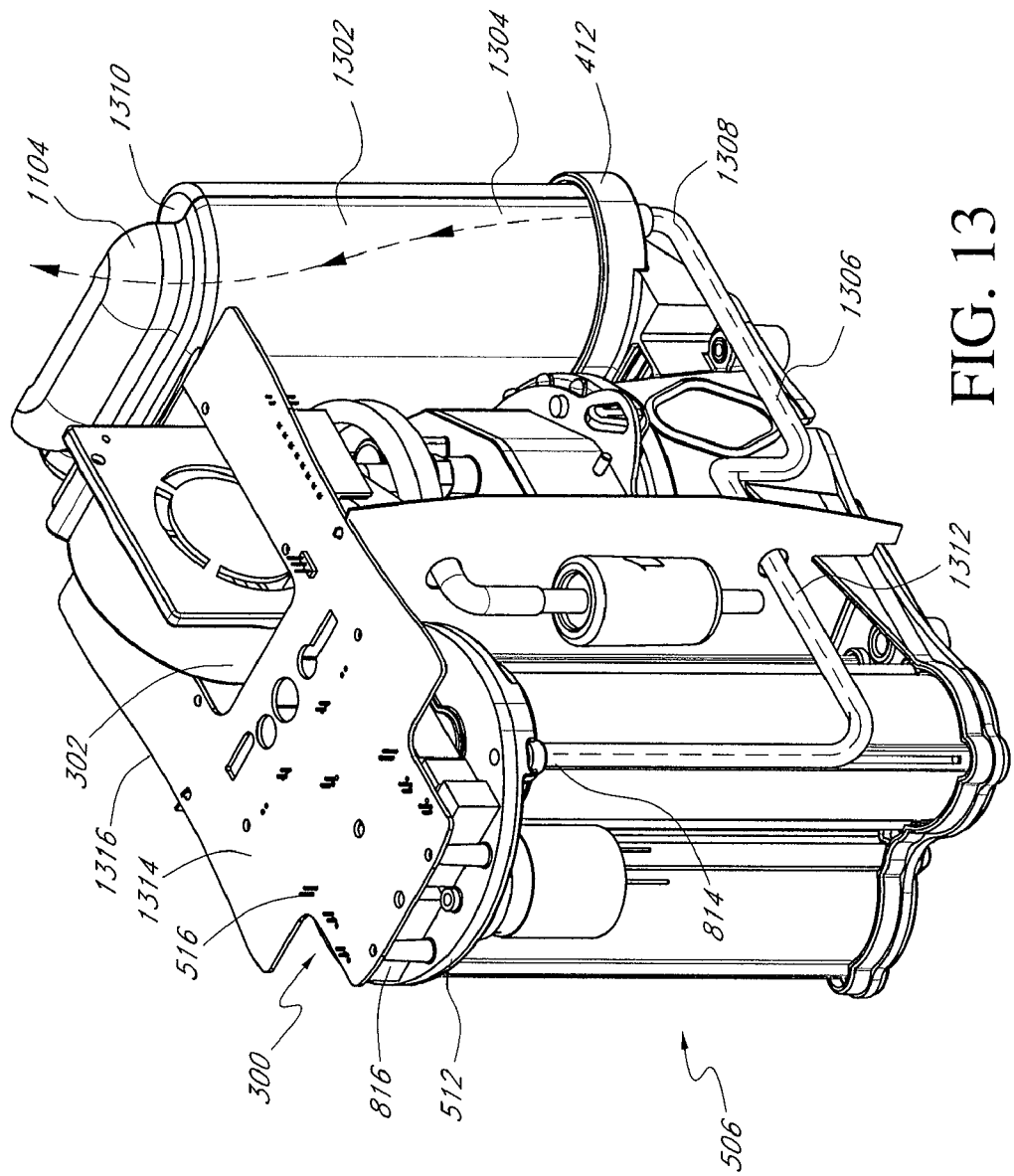
FIG. 13 is a perspective view of the components assembled in the housing of the apparatus of FIG. 2.

In addition to vibration control features, the apparatus also incorporates one or more thermal management systems to provide cooling for temperature sensitive components inside the housing and facilitate heat dissipation. FIG. 13 illustrates a thermal management system of one preferred embodiment adapted to provide cooling for the battery. A thermal sleeve 1302 is positioned around the battery 1104 to isolate air surrounding the battery 1104 from higher temperature air in the second compartment 302 of the housing. A lower end 1304 of the thermal sleeve 1302 is configured to mate with the battery slot 412 so as to close off the lower opening of the sleeve and form a compartment or air pocket for the battery. A cooling gas is preferably directed into the space between the thermal sleeve 1302 and the battery 1104 to facilitate dissipation of heat generated by the battery and also to insulate the battery from heat generated by other components in the housing.

In one embodiment, a conduit 1306 extends from the exhaust outlet 814 of the PSA unit 506 to an opening 1038 in the battery slot 412. The conduit 1306 directs exhaust gas 1312 from the PSA unit 506 into the space between the thermal sleeve 1302 and the battery 1104. Since the exhaust gas is typically cooler than ambient air surrounding the battery compartment, it serves as an efficient source of cooling air for the battery. The exhaust gas enters the thermal sleeve 1302 from the lower opening 1308 in the battery slot 412 and circulates out of the upper end 1310 of the thermal sleeve 1302.

As also shown in FIG. 13, a circuit board 1314 is mounted horizontally on the PSA unit 506, above the valves 816 on the manifold 512. The circuit board 1314 comprises control circuitry which governs the operation of the PSA unit, alarms, power management system, and other features of the apparatus. As described above, contacts on the circuit board 1314 are in direct electrical contact with mating contacts 516 on the valves 514 of the PSA unit 506, which conserves space and eliminates the need for wiring connections. In one embodiment, the circuit board 1413 has small through-hole connectors that align with the location of valve pins to establish electrical interconnection.

As will be described in greater detail below, the circuit board 1314 is located in the path of a directed air flow inside the housing so as to facilitate heat dissipation of the circuits during operation. Moreover, although the control circuitry is substantially entirely within the first compartment 300, the circuit board 1314 extends horizontally from the first compartment 300 to the second compartment 302, substantially covering the upper openings of both compartments so as to inhibit migration of higher temperature air from the second compartment 302 into the first 300. In one embodiment, foam material is placed between the outer edges 1316 of the circuit board 1314 and the inner walls of the housing to form an air seal which further inhibits migration of air between the compartments 300, 302. In another embodiment, the circuit board 1314 is shaped to mirror the cross-sectional contour of the housing so as to ensure an effective seal between the circuit board 1314 and housing.

Figure 14:
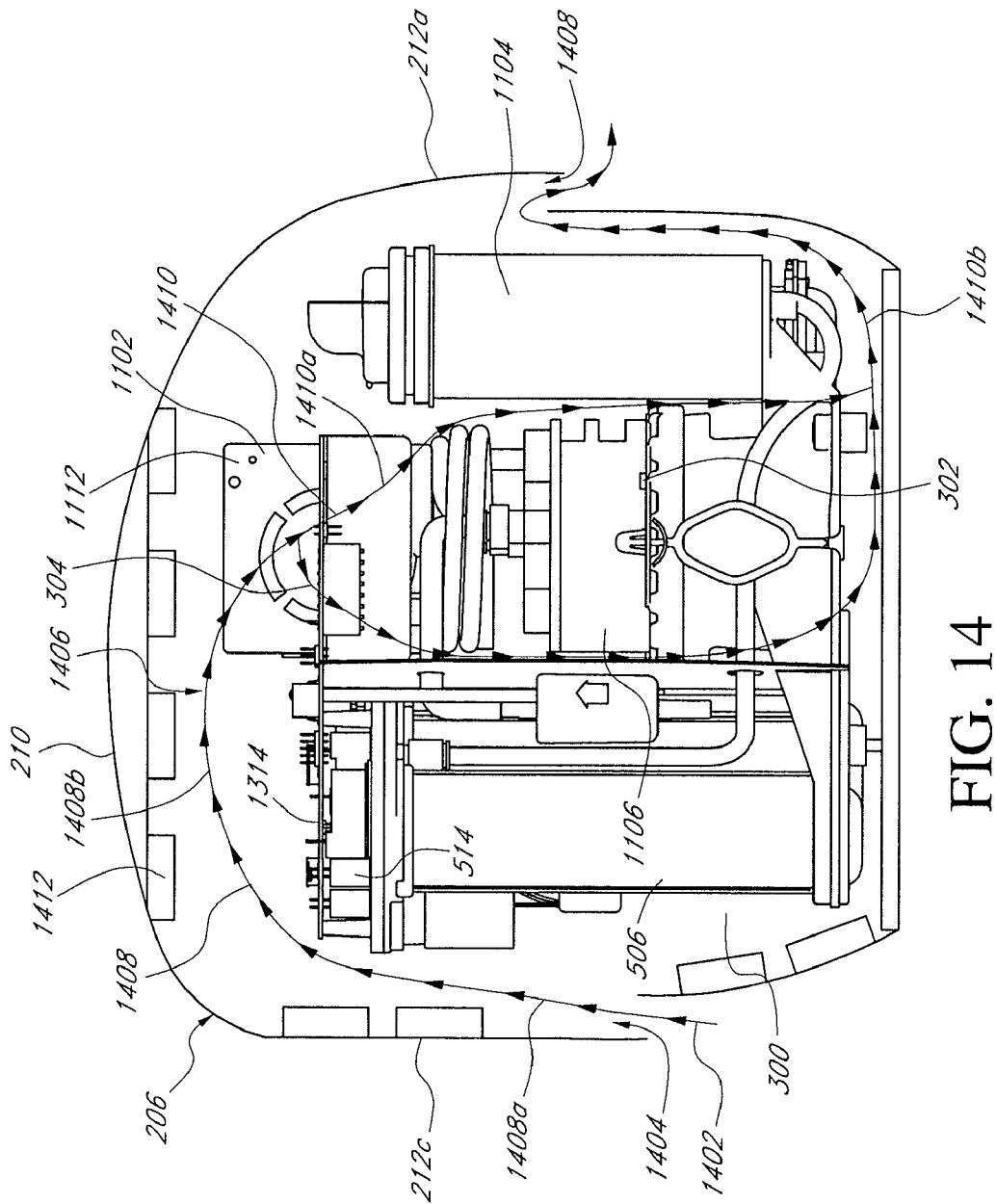
FIG. 14 is a schematic diagram of a directed ambient air flow through the housing of the apparatus of FIG. 2, illustrating a thermal management system of one preferred embodiment.

FIG. 14 schematically illustrates a thermal management system of another preferred embodiment, which is configured to provide a continuous flow of cooling air across the components inside the housing. As shown in FIG. 14, ambient air 1402 is drawn into the housing 206 through an air inlet 1404 by the fan 1102. The air inlet 1404 is preferably located in a lower portion of the sidewall 212c adjacent the first compartment 300. The ambient air 1402 is direct to flow through an air flow passageway 1406 generally defined by the walls of the housing and the components therein. The air flow passageway 1406 is preferably a circuitous path extending from the air inlet 1404, through the first and second compartments 300, 302, to an air outlet 1408 located in a lower portion of the sidewall 212a adjacent the second compartment 302. Preferably, the ambient air is directed to flow across the first compartment, which contains temperature sensitive components, before entering the second compartment which contains heat generating components. As will be described in greater detail below, the thermal management system utilizes the air circulation fan 1102 in combination with the configuration of the housing and placement of components therein to produce a one-way flow passageway for air from inlet to outlet. As such, heated air is not re-circulated back into the system and the components are cooled by a continuous stream of external air.

In one embodiment, the air flow passageway 1406 has an upstream portion 1408 and a downstream portion 1410. The upstream portion 1408 includes a vertical path 1406a generally defined by the PSA unit 506 and the sidewall 212c of the housing 206 followed by a horizontal path 1406b generally defined by the circuit board 1314 and the upper wall 210. The downstream portion 1410 includes a vertical path 1410a generally defined by the partition 304 and the battery 1104, a horizontal path 1410b generally defined by the compressor assembly 1106 and the base 208 of the housing, and followed by another vertical path 1410c defined by the battery 1104 and the sidewall 212a. Air in the upstream portion 1408 of the passageway 1406 preferably has a lower temperature than air in the downstream portion 1420 where most heat generating components are located. Temperature sensitive components such as the valves 514 and electrical components disposed on the circuit board 1314 are advantageously disposed in the upstream portion 1408, thereby exposing the valves and components to a continuous stream of incoming cooling air, which reduces their thermal load. Preferably, the upstream portion 1408 of the air flow passageway 1406 is thermally isolated from the downstream portion 1410 by the partition 304 and the circuit board 1314 in conjunction with a directed air flow described below.

As also shown in FIG. 14, the fan 112 is located in the downstream portion 1410 of the air flow passageway 1406 immediately above the compressor assembly 1106. The fan 112 generates a downward air stream directly against the compressor assembly 1106 to facilitate heat dissipation of the heat exchanger and compressor. The air stream flows past the compressor assembly 1106 through the downstream portion 1410 of the air passageway 1406 and exits the housing 206 through the air outlet 1408. The fan 1102 is advantageously positioned to focus a cooling air stream directly on the heat generating components inside the housing. Moreover, portions of the air stream warmed by the compressor assembly are not re-circulated inside the housing, which substantially minimizes increases in the ambient temperature therein and improves cooling efficiency. The air stream generated by the fan 1102 creates a negative pressure in the upstream portion of the passageway 1406, which draws ambient air through the passageway 1406 from the first compartment 300 to the second compartment 302 as shown in FIG. 14. Although some turbulence of the air may occur downstream of the fan, the air path configuration permits substantially one way air flow along the path between the intake and the fan.

In certain embodiments, noise reduction features are also implemented in the apparatus. As shown in FIG. 14, a series of sound absorbing baffles 1412 are positioned along the air flow pathway 1406 to reduce noise caused by the air flow inside the housing. Moreover, the air flow passageway is configured with a circuitous path so as to further abate the noise generated by the air flow. The circuitous path advantageously provides for air movement through the housing, but makes it difficult for sound to propagate or reflect off internal surfaces of the housing and make its way out of the housing.

Figure 15:
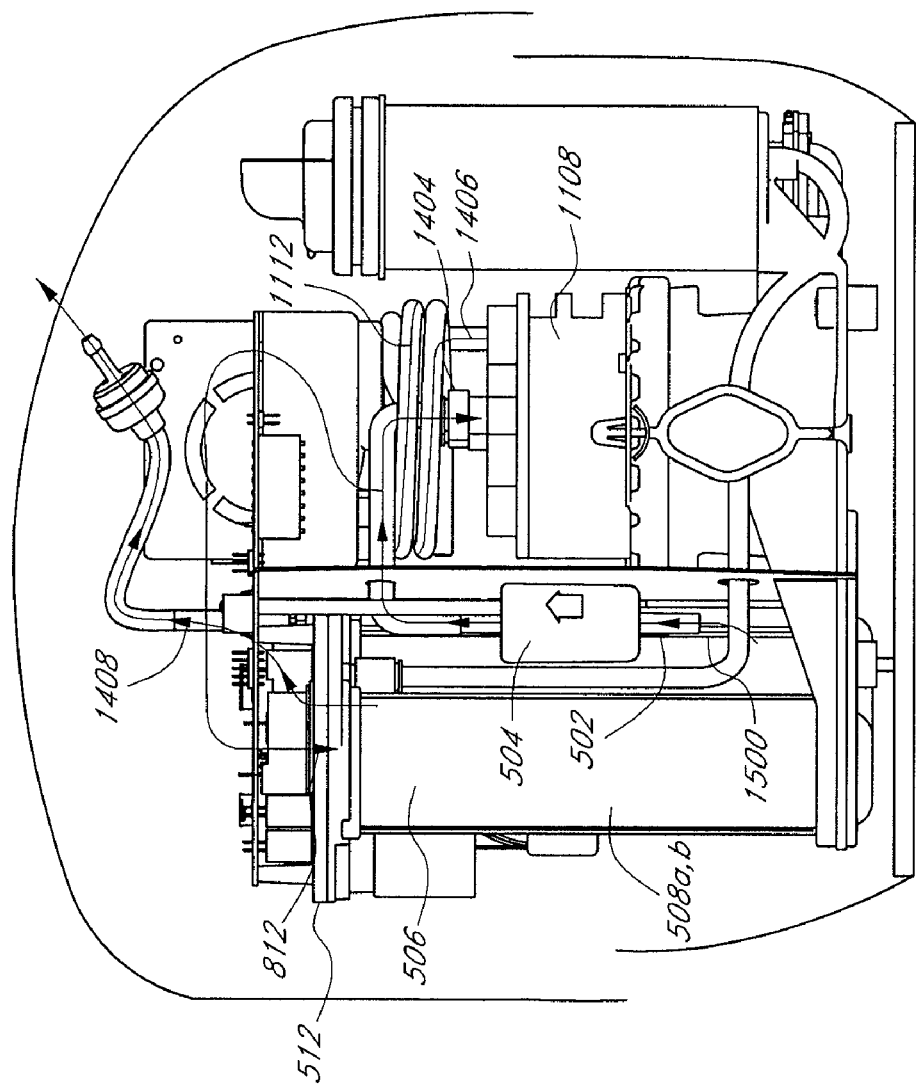
FIG. 15 is a schematic diagram of a gas flow through the components of the apparatus of FIG. 2.

FIG. 15 schematically illustrates the manner in which intake air 1500 is processed through the components of the apparatus. As shown in FIG. 15, intake air 1500 is drawn through the air intake 502, through the air filter 504 into an inlet port 1404 of the compressor 1108. Air is preferably drawn into the compressor air intake at a flow rate of no greater than about 15 slpm so as to maintain a low noise level and low power consumption throughout the system. The air is pressurized by the compressor 1108 and delivered to the heat exchanger 1112 through the compressor outlet 1406. The pressurized air is cooled by the heat exchanger 1112 and then supplied as feed gas to the PSA unit 506. Feed gas is directed through the inlet port 812 of the PSA unit 506, into adsorbent columns 508a-b to produce a product gas in accordance with a PSA cycle, preferably the six step/two bed cycle described above. Product gas from the adsorbent columns 508a-b flows into the storage column and is delivered to the patent through an outlet port 1408 in the manifold 512 connected to the storage column. Preferably, the product gas is delivered to the patient at a flow rate of between about 150 ml/minute and 750 ml/minute and having an oxygen concentration of at least 87%, more preferably between 87%-93%.

Figure 16A:
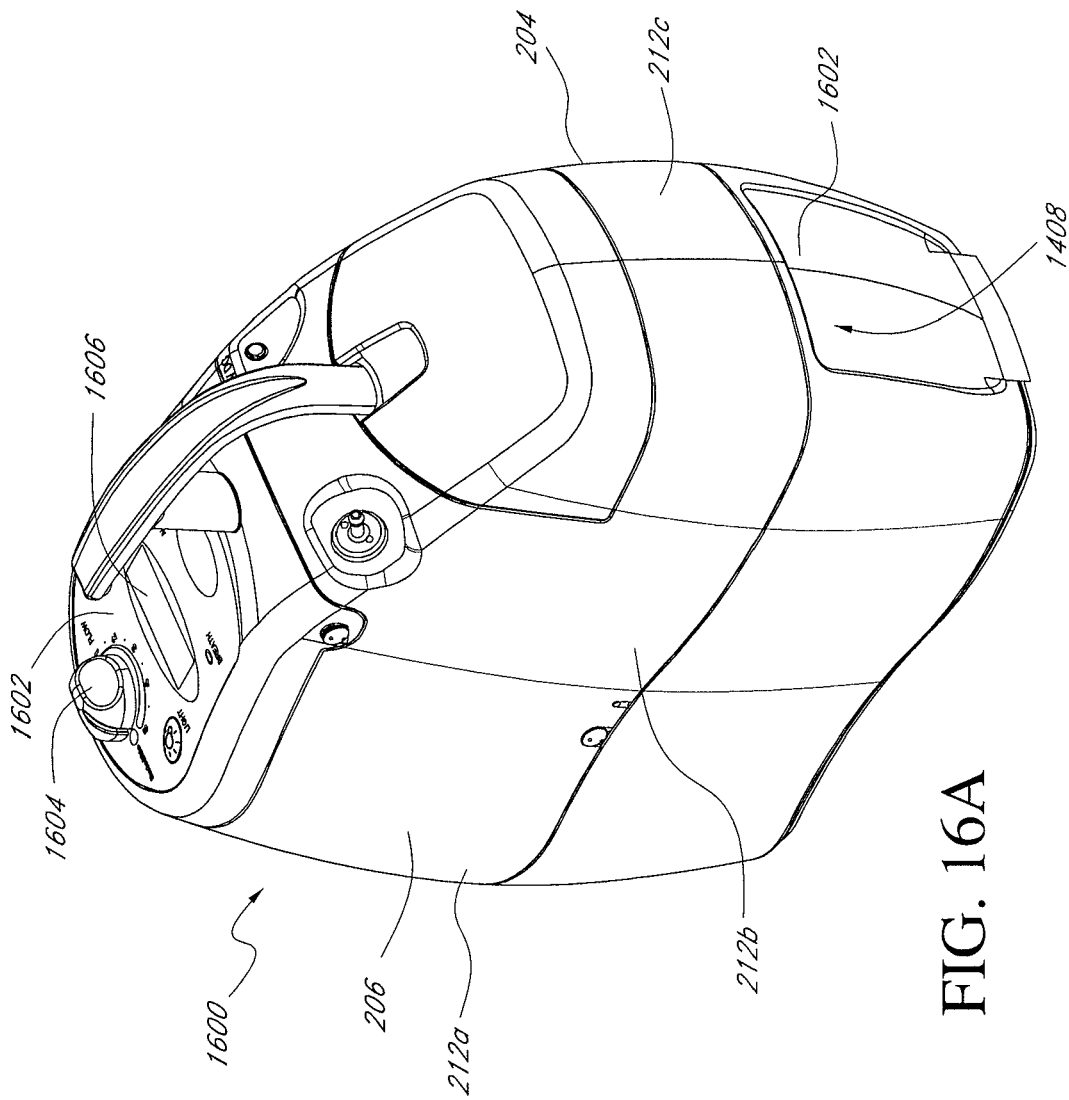
FIG. 16A is a perspective view of the apparatus of FIG. 2, showing an in-line filter integrated in the shell of the apparatus.

FIG. 16A shows the apparatus as fully assembled in the form of a portable oxygen concentrator unit 1600. The unit 1600, including the housing and components therein, has a combined weight of preferably no than about 10 pounds and produces a noise level of no greater than about 45 dB external to the unit. As shown in FIG. 16A, an air scoop 1602 is integrally formed in the sidewall 212 c of the shell 204 adjacent the air outlet 1408 to channel air flow out of the housing 206. A similar air scoop is also formed in the sidewall adjacent the air inlet (not shown) to channel ambient air into the housing. As described above, the sidewalls 212a, c of the housing have a curved configuration so as to discourage users from resting the housing against the sidewall, which can block the air inlet or outlet.

As also shown in FIG. 16A, a user interface panel 1602 containing a plurality of system controls 1604 such as flow rate and on-off switches is integrally formed in the shell 204. In some embodiments, an I/O port 1606 is preferably formed in the user interface panel 1602. The I/O port allows data transfer from the unit to be performed simply by using a complementary device such as a palm desktop assistant (PDA) or laptop computer. Moreover, an in-line filter system 1608 is also formed in the shell 204 to filter product flow in line prior to delivery to the patient. As will be described in detail below, the in-line filter system 1608 is integrated in the shell 206 of the unit so as to provide easy access to the filter without requiring opening of the shell.

Figure 16B:
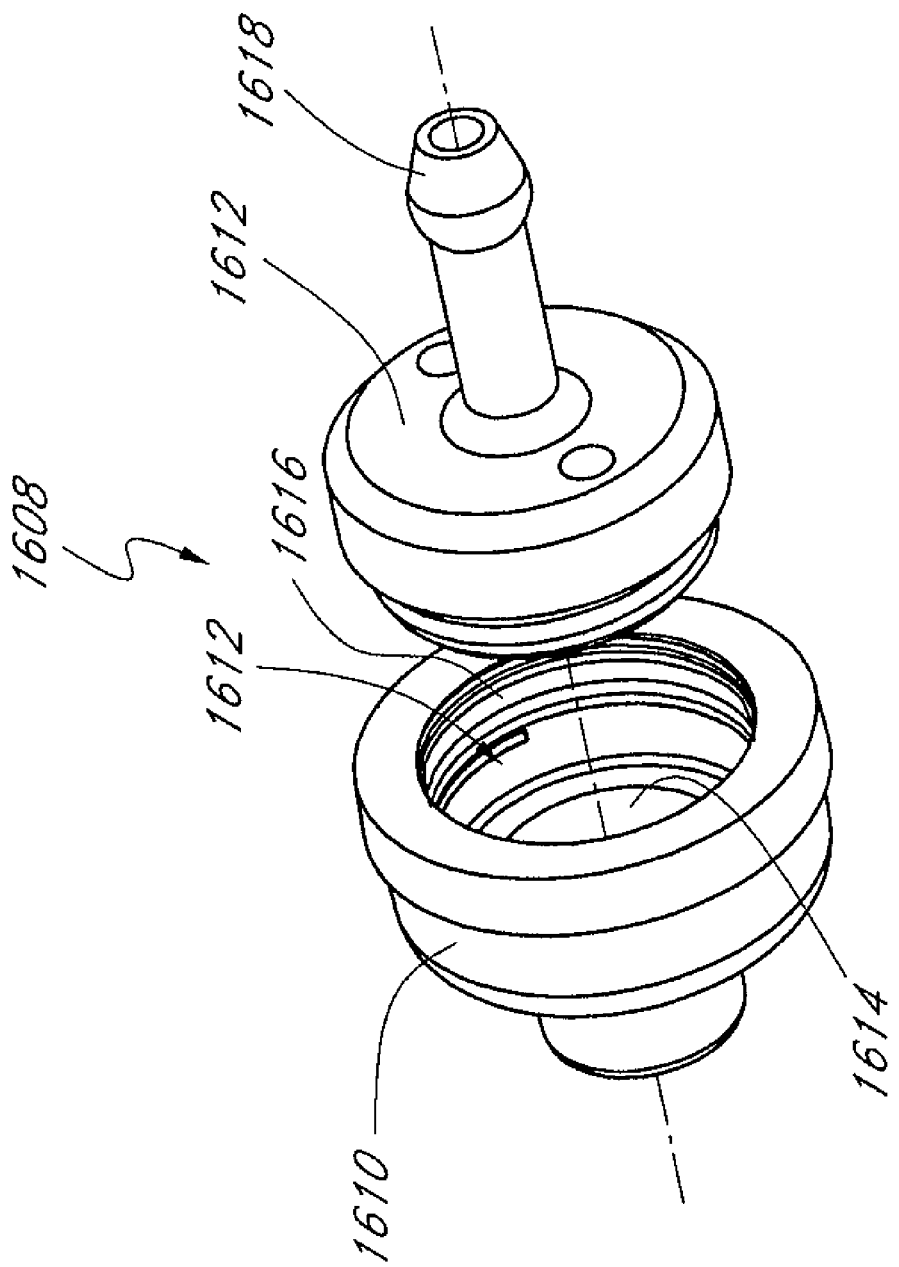
FIG. 16B is a detailed view of the in-line filter of FIG. 16B.
Figure 16C:
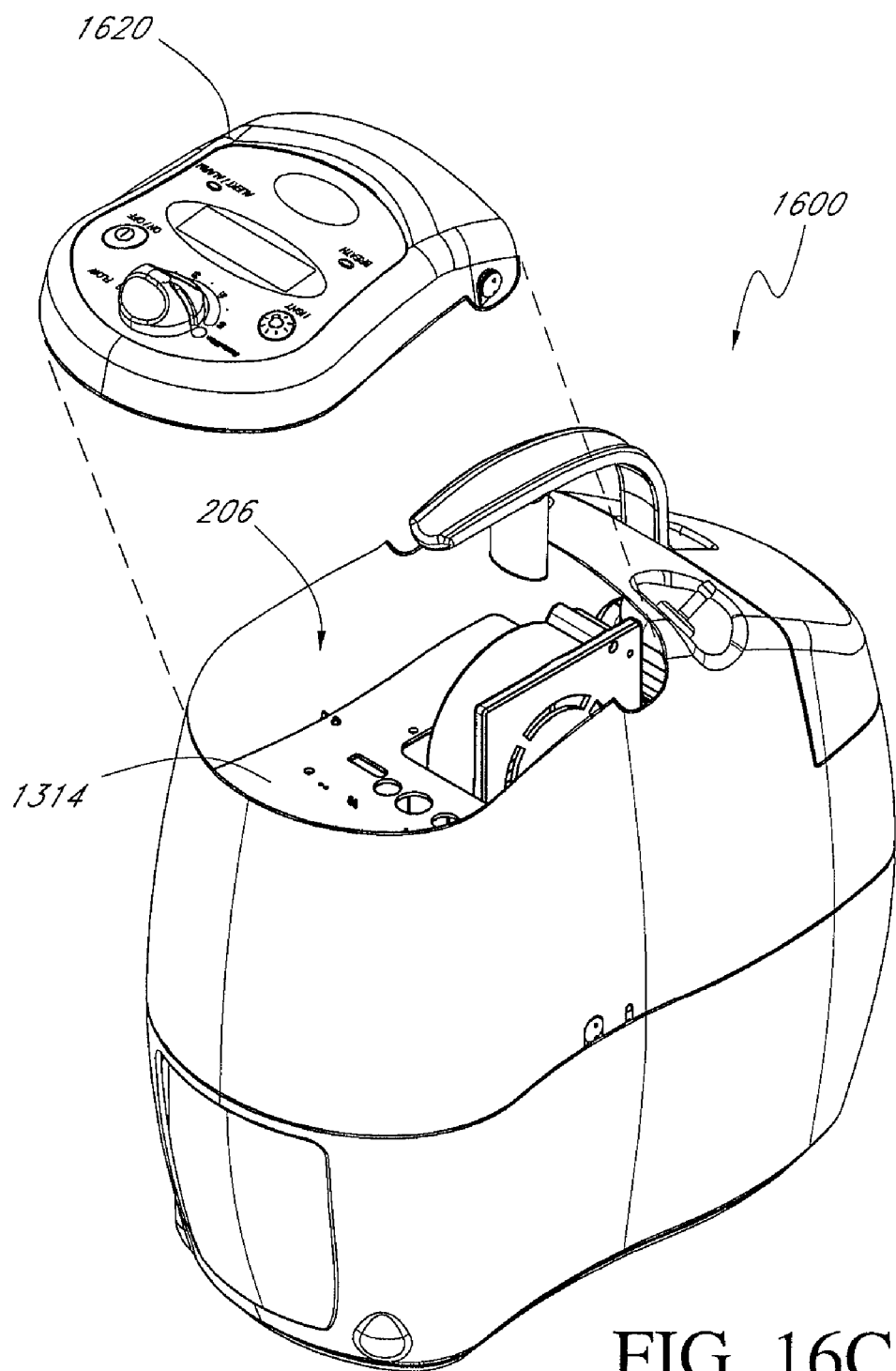
FIG. 16C is a perspective view of the apparatus of FIG. 2, showing a removable hatch.

As shown in FIG. 16B, the in-line filter system 1608 includes an annular chamber 1610 formed in the shell 204 and a fitting 1612 that engages with the chamber 1610 from outside of the shell. The chamber 1610 has a seat portion 1612 configured to receive a disk filter 1614 and a threaded portion configured to engage with the fitting 1612. Preferably, the chamber 1610 is molded into the shell 204 and oxygen product inside the housing is ported to the chamber. In one embodiment, the disk filter 1614, preferably a 10 micron or finer filter, is held in compression in the seat portion 1612 of the chamber by the fitting 1612, which threadably engages with the chamber 1610 from outside of the shell. In another embodiment, the fitting 1612 also contains a hose barb 1618 used to connect the cannula. Advantageously, the disk filter 1614 can be serviced by simply unscrewing the fitting 1612, replacing the filter 1614, and then re-screwing the fitting 1612 without ever having to open the housing of the unit. As shown in FIG. 16C, the unit 1600 also includes a removable hatch 1620 that provides simplified access to the circuit board 1314 inside the housing 206 and the internal connections to the oxygen product line and power input.

Figure 17:
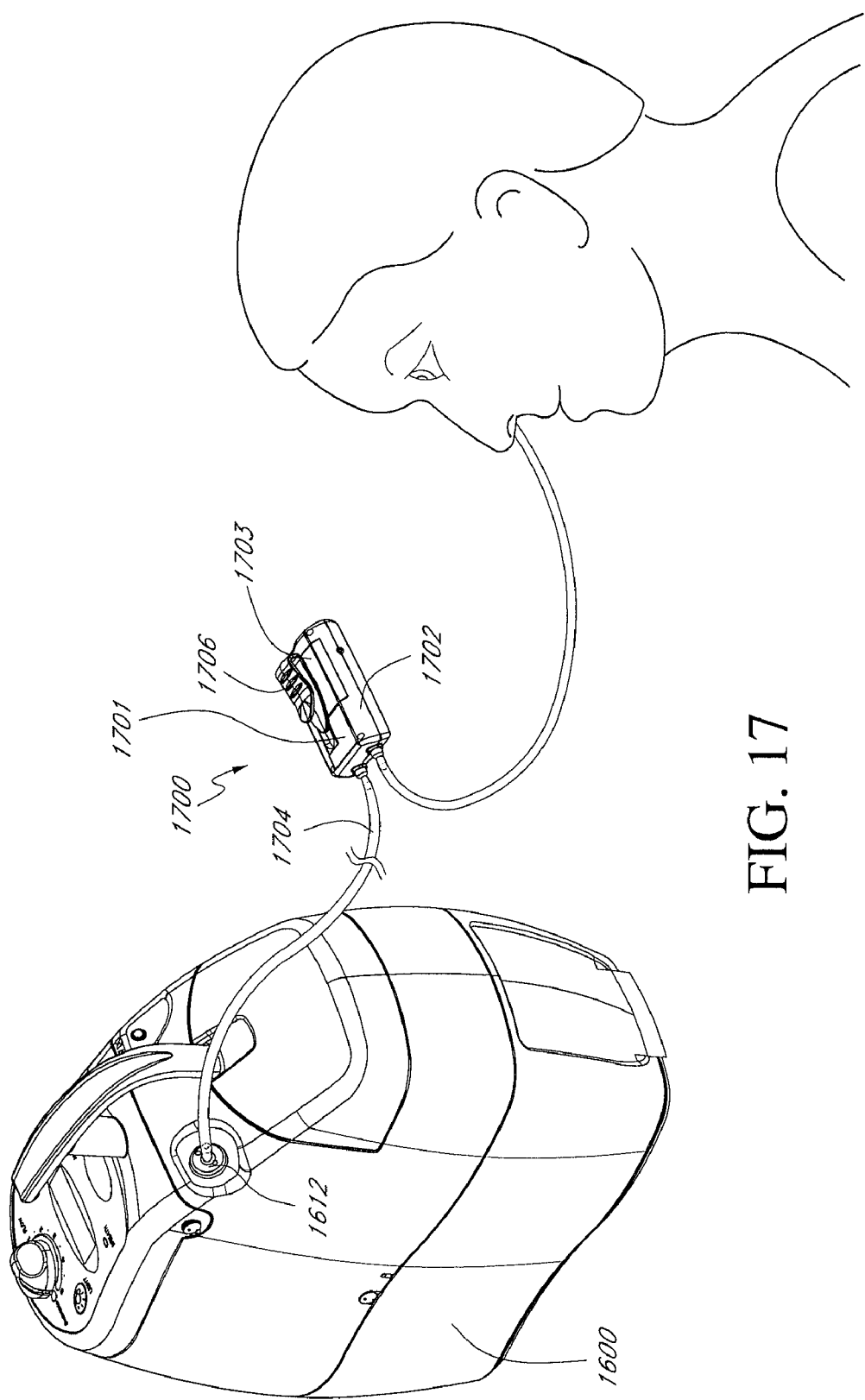
FIG. 17 is a schematic illustration of a satellite conserver used in conjunction with the apparatus of FIG. 2.

FIG. 17 schematically illustrates a satellite conserver system 1700 that can be used in conjunction with the oxygen concentrator unit 1600 to deliver oxygen to users. It is generally recognized that oxygen concentrators deliver a finite rate of oxygen product which must be metered to the user through a conserving device. A conserving device is typically mounted inside the concentrator and includes a breath sensor that senses breath inhalation of the user to determine the timing and quantity of each bolus delivery. The sensitivity of the breath sensor is significant to the efficacy of the conserving device. As such, most conserving devices require that users use no longer than a 10 feet tube connected to the nasal cannula to ensure that the conserving device inside the concentrator can accurately sense the breath of the user.

The satellite conserver 1700 is configured to substantially remove the constraint imposed by the short tube requirement and allow users the freedom to move in a much larger area around the portable concentrator. As shown in FIG. 17, the satellite conserver 1700 includes a small, lightweight conserving device 1702 for delivering oxygen rich product gas to users in metered amounts in a known manner in response to sensed breath. The conserver 1700 includes a breather sensor 1701 for sensing the user's breath and a delivery valve 1703 for delivering oxygen to the user. In one embodiment, the conserving device 1702 utilizes a breath rate algorithm that delivers a nearly constant amount of oxygen per minute, regardless of the breath rate of the patient. As such, patients who take more breaths within a give time period receive the same amount of oxygen as those who take less breaths. In another embodiment, the conserving device adjusts the bolus volume based on the flow setting rather than the breathing rate. In yet another embodiment, the conserving device 1702 can be fit with a second pressure sensor, which detects the pressure in the input line from the concentrator. The delivery valve timing can be adjusted based on the sensed pressure at the end of the input line such that a higher pressure corresponds to a shorter valve open time and a lower pressure corresponds to a longer valve open time.

As also shown in FIG. 17, the conserving device 1702 is adapted to be worn by the user or positioned adjacent to the user so that breath sensing functions can be performed proximate to the user even if the concentrator unit is far away. Thus, the sensitivity of the breath sensor is not compromised even if the user is far way from the unit. The satellite conserver 1700 further includes flexible tubing 1704 connecting the conserving device 1702 to the hose barb fitting 1612 on the concentrator 1600. In one embodiment, the tubing 1704 is preferably between 50 to 100 feet, which provides users a much greater radius of mobility. When the satellite conserver 1700 is in use, the breath detector mounted inside the housing of the concentrator is disabled. As also shown in FIG. 17, the satellite conserver can be worn on the person by a clip 1706 attached to the conserving device 1702. The satellite conserver advantageously permits the user to move around the vicinity of the concentrator, preferably in at least a 50 to 100 feet radius, without detracting from the efficacy of the unit.

Figure 17A:
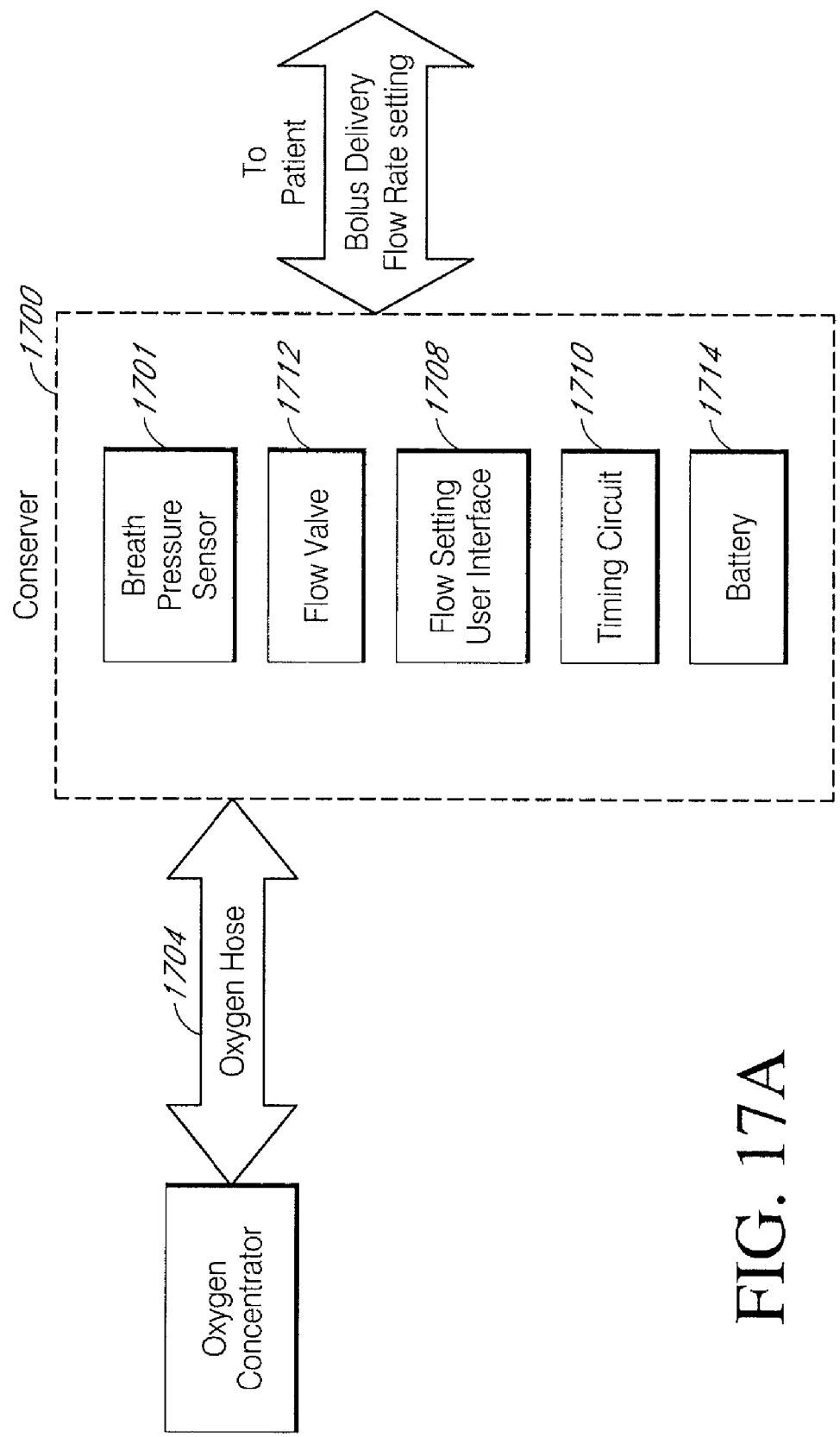
FIG. 17A illustrates the various functionalities including flow setting user interface incorporated in the satellite conserver of FIG. 17.

To further add to the convenience of the patient, it is desirable to add in some level of patient control of the concentrator functionality in the satellite conserver 1700. For cases where the patient is using a long hose between the satellite conserver and the concentrator, it is advantageous to allow the patient to change some settings without the necessity of returning to the concentrator base unit. One of the most useful settings to adjust at the conserver is flow rate. If the patient for some reason requires a higher flow rate due to increased exertion while operating at a large distance from the base unit, it would be a problem to require the patient to return to the base unit to obtain a higher flow of oxygen rich air. As shown in FIG. 17A, the satellite conserver device 1700 of certain preferred embodiments includes a patient interface 1708 that allows the patient to change flow rate. One embodiment of this interface is a flow setting knob which selects from several flow rate settings. In one embodiment, the knob interfaces to a timing circuit 1710. The timing circuit 1710 controls how long a flow valve 1712 is open. Thus when the breath sensor 1701 detects a breath, the flow valve 1712 is opened for a time determined by the knob setting. In certain embodiments, the conserver requires a battery 1714 to power the timing circuit sensor 1710 and valve 1712.

Figure 18A:
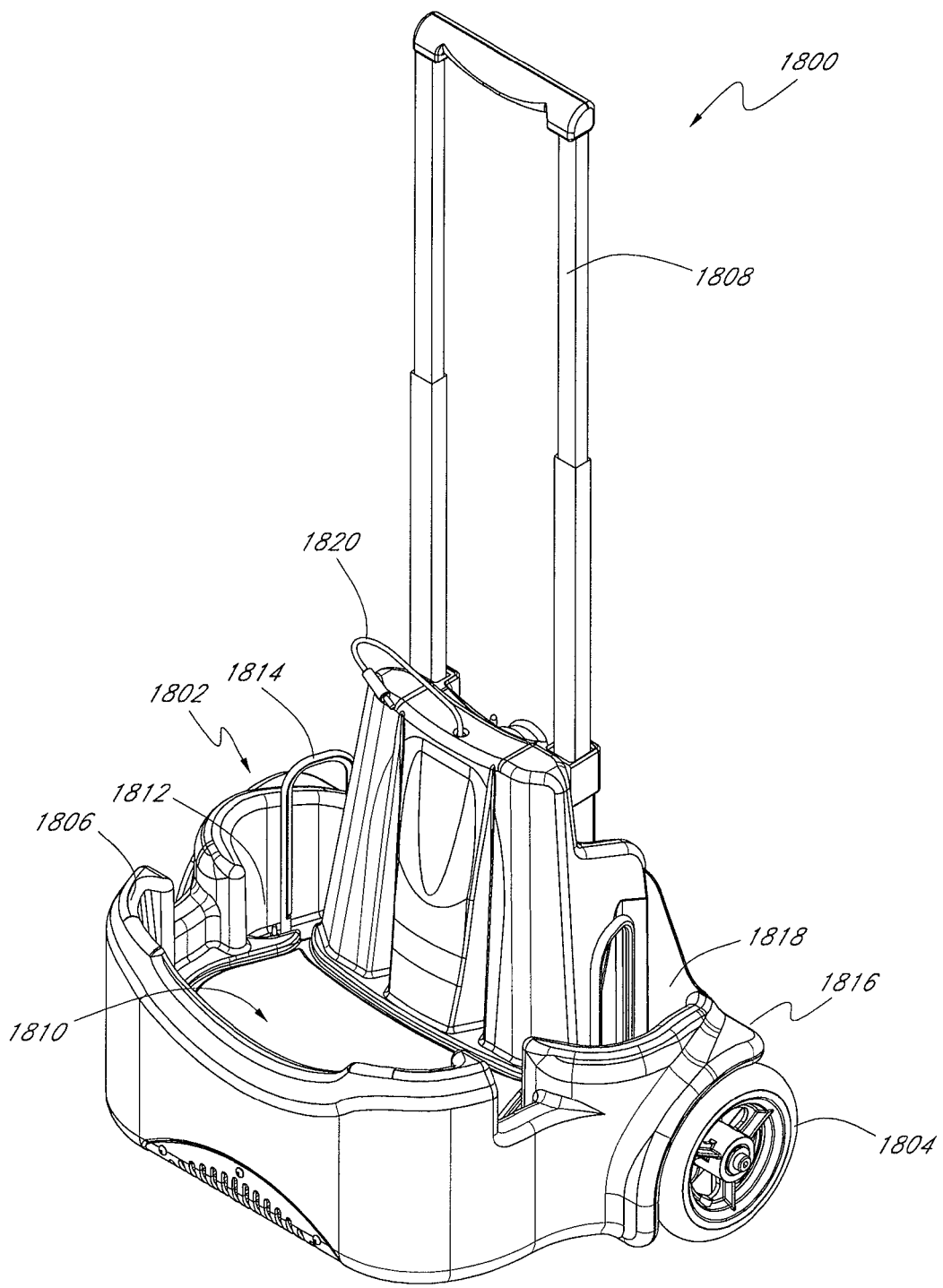
FIGS. 18A and 18B are schematic illustrations of a mobility cart used in conjunction with the apparatus of FIG. 2 for transporting the apparatus.

FIG. 18A schematically illustrates a mobility cart 1800 configured to transport an oxygen concentrator unit for users traveling away from home. As shown in FIG. 18A, the mobility cart 1800 includes a generally rectangular frame 1802 attached to a plurality of wheels 1804 so as to permit rolling movement of the frame 1802 over the ground. As also shown in FIG. 18A, the frame 1802 has a support portion 1806 adapted for receiving an oxygen concentrator unit and a handle portion 1808 extending upwardly from the support portion 1806 for users to hold when moving the cart. The support portion 1806 preferably contains a compartment 1810 configured to seat the oxygen concentrator and at least two slots 1812 configured to seat and secure spare batteries. In one embodiment, a battery bail 1814 is placed in each slot 1812 for securing the batteries in the manner described above. In another embodiment, a small recess 1816 is formed in the back of the compartment 1810 for holding the satellite conserver, spare cannulas or filter.

As also shown in FIG. 18A, the mobility cart 1800 further includes an on-board power supply 1818 that is attached to the frame 1802 portion. Preferably, the power supply 1818 has an AC power input and is adapted to power charging terminals fitted in each battery slot 1812 and a terminal fitted in the compartment 1810 for charging the battery within the concentrator. In one embodiment, the cart also has an adapter plug 1820 that extends from the power supply 1818 and mates with the concentrator's DC power input jack. The power supply 1816 is preferably sufficient to power both battery chargers while simultaneously powering the concentrator unit and charging the battery mounted inside the unit. Each battery preferably has a rated life of at least 2 hours so that the user is able to enjoy continuous use of the concentrator unit for at least six hours without an external power source. In one embodiment, the power supply is cooled by a fan mounted on the frame portion 1802. In another embodiment, the frame portion has recesses through which water may drain out without damaging the parts. The cart 1800 can further comprise an integrated power cord and/or retractable power cord that is adapted to be plugged into a wall.

Figure 18B:
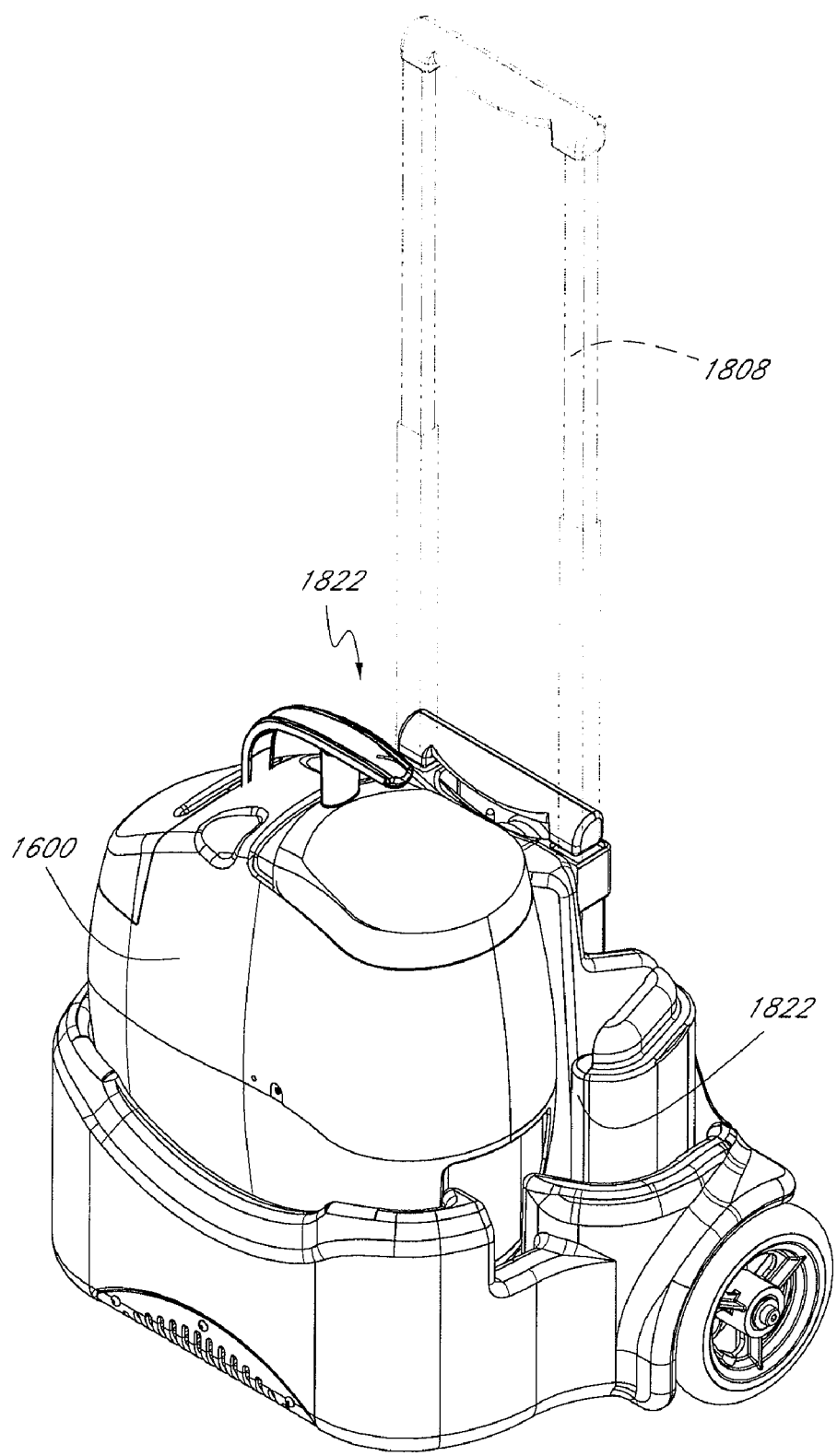

FIG. 18B illustrates the manner in which the oxygen concentrator 1600 and spare batteries 1822 are positioned in the mobility cart. As also shown in FIG. 18B, the handle 1808 has two telescoping rails that can be extended and retracted. When the handle 1808 is the fully retracted position as shown in FIG. 18B, the mobility cart 1800 preferably has a height of about 14-18 inches and can be stored in a small area such as under an airplane seat. In one embodiment, the mobility cart is structured such that the concentrator, when sitting in the cart, interfaces closely with seals positioned on the frame of the cart at the air intake and exhaust ports. As such, airflow coming into or out of the concentrator actually travels through the frame in some manner, adding extra sound attenuation by increasing the tortuosity of the flow path. Moreover, an auxiliary fan or blower mounted in the cart can also be used to circulate this air further. Advantageously, the mobility cart has integrated battery chargers and power supply incorporated in one unit so as to obviate the need for users to pack power supplies or external chargers when traveling with their concentrator. Moreover, the cart provides a single compact unit in which all oxygen concentrator related parts can be transported, which allows users greater ease of mobility when traveling.

Figure 19A:
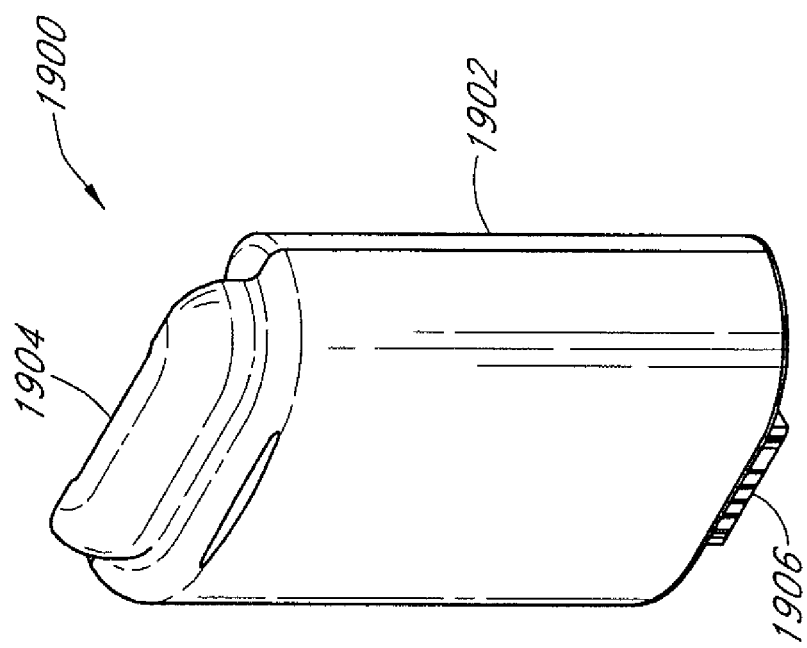
FIG. 19A is a perspective view of a battery pack used to provide electrical power to the portable gas fractionalization apparatus of FIG. 2.

FIGS. 19A-E illustrate a battery pack 1900 configured to provide electrical power to a portable oxygen concentrator of one preferred embodiment of the present invention. As shown in FIG. 19A, the battery pack 1900 has a generally U-shaped body 1902 containing one or more batteries therein, a handle portion 1904 configured to facilitate installation and removal of the battery pack 1900, and a contact protrusion 1906 configured to electrically couple the battery pack 1900 to power contacts on the portable oxygen concentrator. As will be described in greater detail below, the U-shaped body 1902 facilitates proper alignment of the battery pack 1900 to the oxygen concentrator during installation and also helps heat dissipation of the batteries enclosed therein.

Figure 19B:
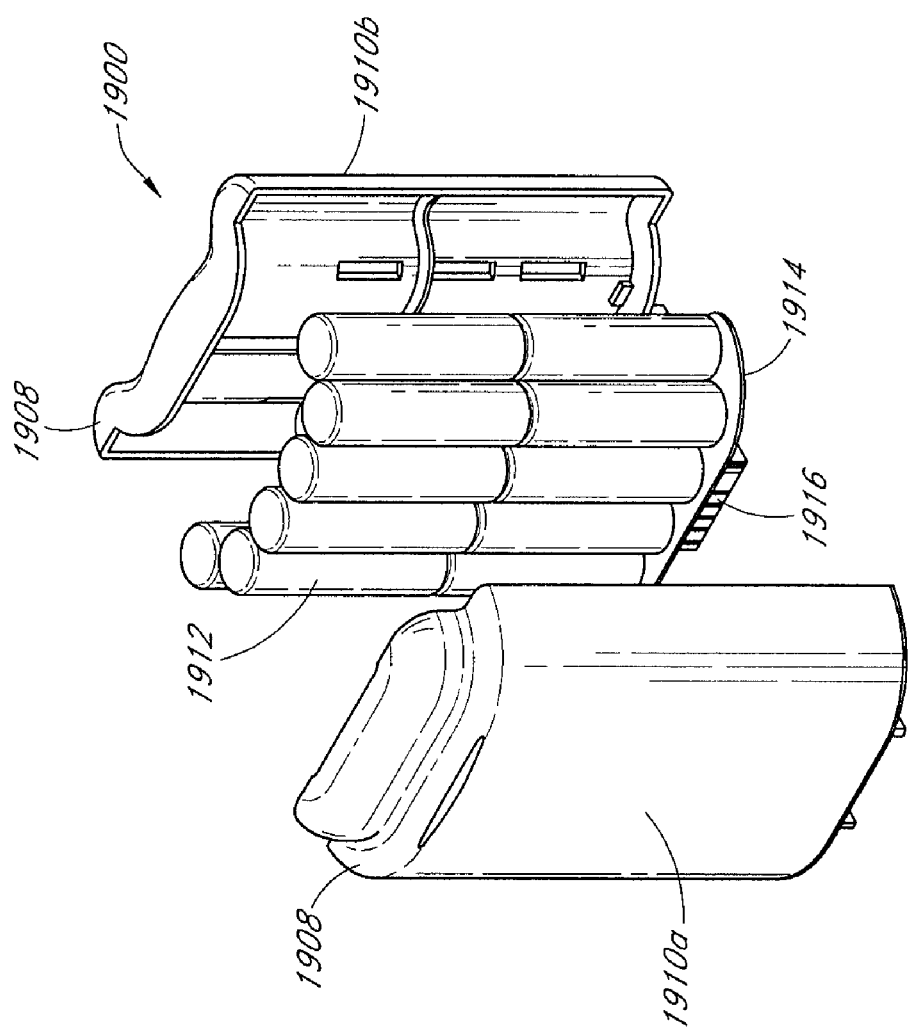
FIG. 19B is an exploded view of the battery pack of FIG. 19A.

FIG. 19B provides an exploded view of the battery pack 1900. As shown in FIG. 19B, the battery pack 1900 generally includes a casing 1908 having two opposing sections 1910a, 1910b and a plurality of battery cells 1912 disposed within the casing 1908. The two opposing sections 1910a, 1910b of the casing 1908 can be joined together by snap fitting, adhesive or other suitable methods. As also illustrated in FIG. 19B, the battery cells 1912 are stacked in a two deep and side-by-side array along a non-linear path, which arrangement facilitates heat dissipation of the batteries without substantially increasing the footprint of the battery pack. In one embodiment, twelve rechargeable lithium ion battery cells 1912 are supported by a base structure 1914 inside the casing 1908. Preferably, the cells are grouped into four sets, with each set containing three cells. The sets are connected in parallel while the cells within each set are connected in series. The battery cells 1912 are also electrically connected to a power contact 1916 that extends outwardly through an opening in the casing 1908 for mating with contacts on the portable oxygen concentrator. Details related to electrical connection of the cells in the battery pack are generally known to persons skilled in the art and thus are not shown and described here. Moreover, it will be appreciated that the batteries used can also include a variety of other known storage cell technology, such as lithium polymer cells, nickel cadmium batteries, and nickel metal hydride batteries.

Figure 19C:
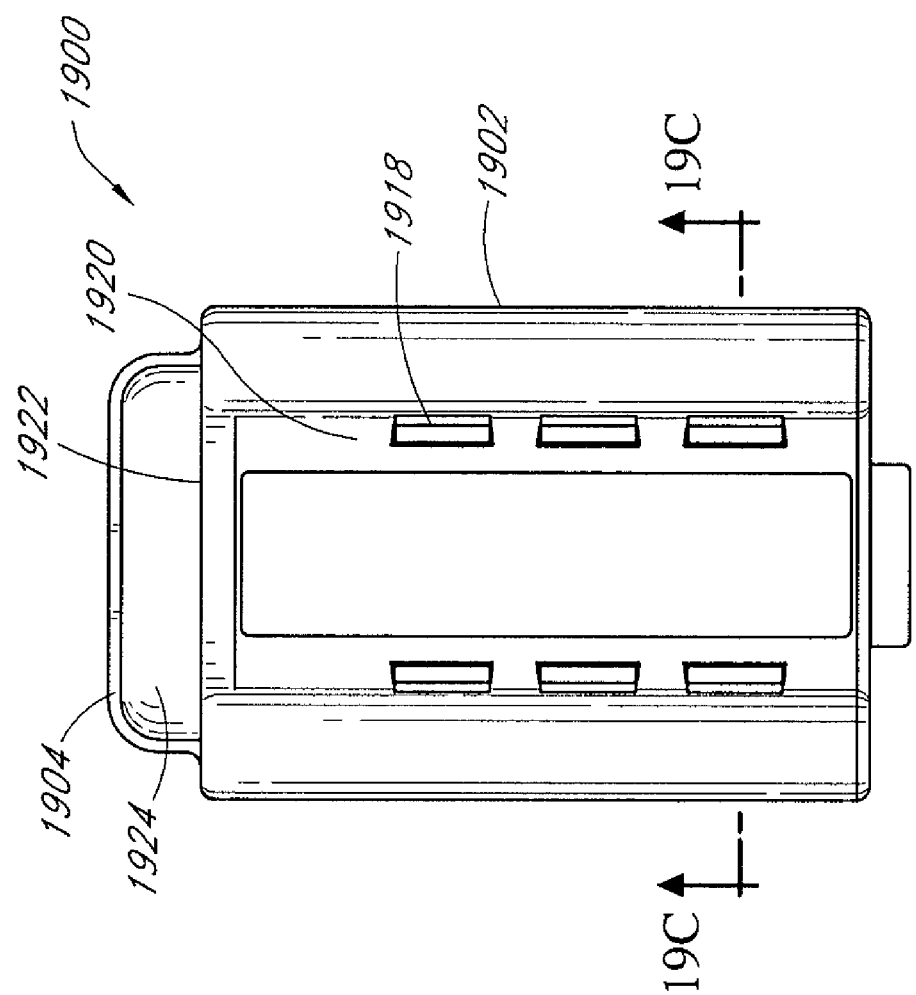
FIG. 19C is a rear view of the battery pack of FIG. 19A.
Figure 19D:
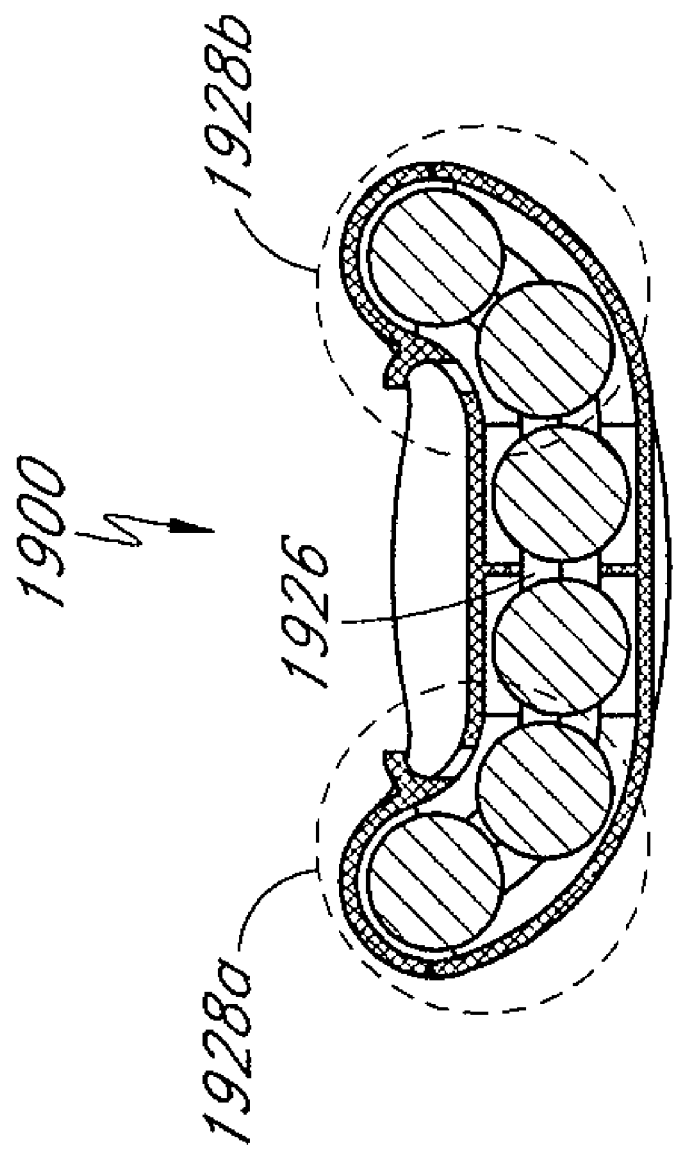
FIG. 19D is a cross-sectional view of the battery pack of FIG. 19A, showing a U-shaped configuration.
Figure 19E:
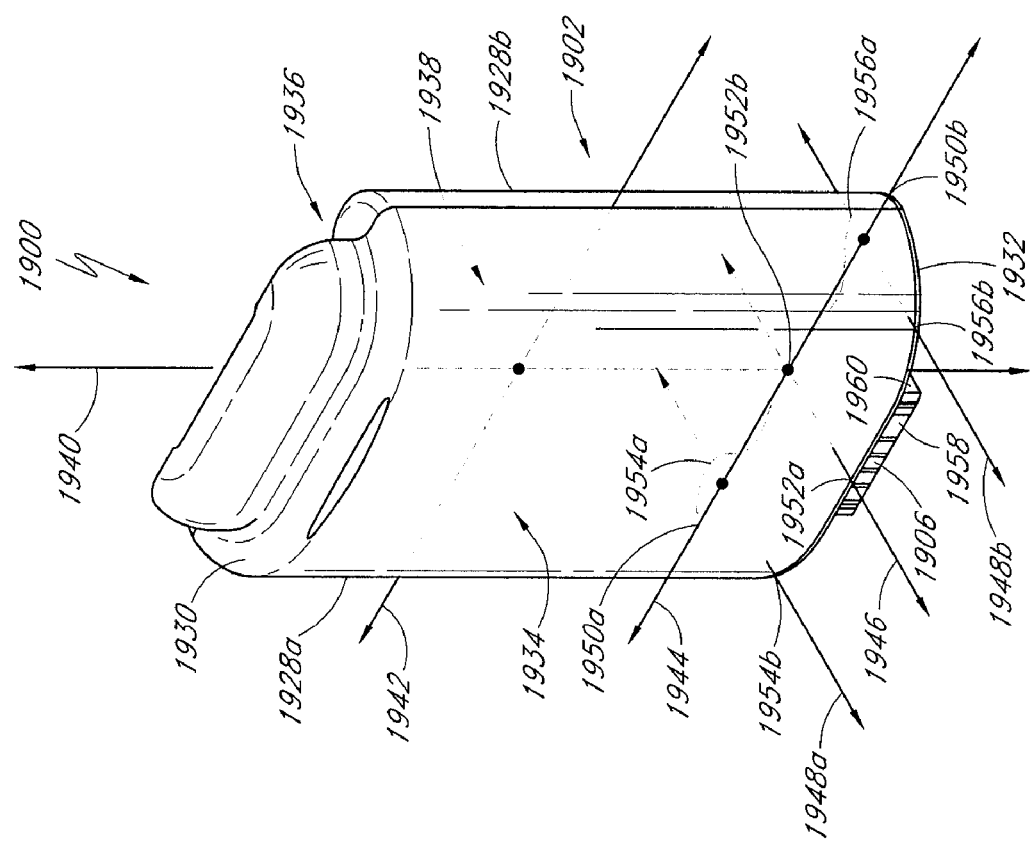
FIG. 19E is a schematic illustration of the battery pack of FIG. 19A.

Referring to FIG. 19C, the battery pack 1900 also includes a plurality of guide rails 1918 formed on an outer surface 1920 of the battery pack 1900. As previously discussed, the guide rails 1918 are configured to engage with a mounting structure on the oxygen concentrator, such as the bail 414 shown in FIG. 4. Preferably, the battery pack 1900 has three pairs of guide rails 1918 with the distance between each pair becoming progressively shorter from bottom to top, with the topmost pair forming the tightest fit with the bail. In one embodiment, the distance between a pair of guide rails is between about 2 to 2.5 inches. As also shown in FIG. 19C, the handle portion 1904 extends from an upper surface 1922 of the battery pack 1900. Preferably, the handle 1904 has a sufficiently large surface area configured for a person to easily grab onto and exert a force against in the vertical direction. In one embodiment, the handle portion 1904 has an elongated concave section 1924 configured to receive a person's fingers so that the person can easily grab onto and lift the battery pack out of the oxygen concentrator. Preferably, the handle portion 1904 has a length of about 4.125 inches or less, a width of about 0.75 inch or less, and a height of about 0.75 inch or less FIG. 19D provides a cross-sectional view of the battery pack 1900. As shown in FIG. 19D, the battery pack 1900 has a generally U-shaped body including a center portion 1926 forming the bight of the U and two end portions 1928a, 1928b projecting from opposite ends of the center portion 1926 forming the legs of the U. The general U-shaped contour of the battery pack 1900 is further illustrated in FIG. 19E. Referring to FIG. 19E, the battery pack 1900 has a top portion 1930, a bottom portion 1932, an exterior side portion 1934, and an interior side portion 1936. The interior side portion 1936 includes at least a portion of the interior sidewall 1938 of the battery pack 1900. The contour of the battery pack 1900 can be further defined by a plurality of axes.

As shown in FIG. 19E, the battery pack 1900 has a longitudinal axis 1940, a transverse axis 1942, a lower transverse axis 1944, a central lower lateral axis 1946 and a first and second end lower lateral axes 1948a, 1948b. The longitudinal axis 1940 is defined as an axis that extends through the top and bottom portions 1930, 1932 and through the interior sidewall 1938 of the battery pack in a manner such that it is generally parallel to the side portions 1934, 1936 and end portions 1928a, 1928b of the battery pack 1900. The transverse axis 1942 is defined as an axis that intersects the longitudinal axis 1940 and extends through the end portions 1928a, 1928b in a manner such that it is generally parallel to the side portions 1934, 1936 and top and bottom portions 1930, 1932 of the battery pack 1900. The lower transverse axis 1944 is defined as an axis that is parallel to the transverse axis 1942, intersects the longitudinal axis 1940 and passes through the bottom portion 1932 of the battery pack 1900. The central lower lateral axis 1946 is defined as an axis that is orthogonal to the longitudinal axis 1940 and intersects both the longitudinal axis 1940 and the lower transverse axis 1944. The first and second end lower lateral axes 1948a, 1948b are defines as axes that are parallel to the central lower lateral axis 1944, intersect the lower transverse axis 1944, and pass through the respective end portions 1928a, 1928b.

In a preferred embodiment, the distance between the exterior surfaces 1950a, 1950b of the end portions 1928a, 1928b measured along the lower transverse axis 1944 is about 4.25 inches or less; the distance between the exterior surfaces 1952a, 1952b of the side portions 1934, 1936 along the central lower lateral axis 1946 is about 1 inch or less; the distance between the exterior surfaces 1954a, 1954b of the first end portion 1928a along the first end lateral lower axis 1948a is about 1.5 inches or less; and the distance between the exterior surfaces 1956a, 1956b of the second end portion 1928b along the second end lateral lower axis 1948b is also about 1.5 inches or less.

As also shown in FIG. 19E, the contact protrusion 1906 has a rectangular shape generally defined by two pairs of opposing sidewalls 1958, 1960. The sidewalls 1958, 1960 preferably extend outwardly from the bottom portion 1932 by about ⅜ inch or more. The length of the sidewalls 1958 that are parallel to the lower transverse axis 1944 is about 1.5 inch or less. The length of the sidewalls 1960 that are parallel to the central lower lateral axis is about 0.5 inch or less. The contact protrusion 1906 is configured be received into a recess on the oxygen concentrator and mate with power contacts therein to electrically connect the battery pack to the concentrator. Alternatively, the contact protrusion 1906 can also be received into a recess formed in a mobility cart or in a separate battery charger to mate with power contacts therein. Preferably, the battery pack 1900 is symmetrical about the center lower lateral axis 1946 but asymmetrical about the lower transverse axis 1944. The asymmetrical configuration functions as a key for users to properly align the battery pack in the oxygen concentrator.

Although the foregoing description of certain preferred embodiments of the present invention has shown, described and pointed out the fundamental novel features of the invention, it will be understood that various omissions, substitutions, and changes in the form of the detail of the system, apparatus, and methods as illustrated as well as the uses thereof, may be made by those skilled in the art, without departing from the spirit of the invention. Consequently, the scope of the present invention should not be limited to the foregoing discussions.

What is claimed is:

1. A battery pack for providing electrical power to a portable oxygen concentrator, comprising:

a generally U-shaped body defined by a center portion and end portions, said center portion forms the bight of the U and said end portions form the legs of the U;

a top portion, a bottom portion, an exterior side portion and an interior side portion;

a longitudinal axis, said longitudinal axis is an axis that extends through the top and bottom portions and generally parallel to the side and end portions and passing through a wall of the interior side portion;

a transverse axis, said transverse axis is an axis that extends through the end portions and parallel to the side, bottom, and top portions and intersecting the longitudinal axis a lower transverse axis, said lower transverse axis is an axis that is parallel to the transverse axis and passing through the bottom portion and intersecting the longitudinal axis;

a central lower lateral axis, said central lower lateral axis is an axis orthogonal to the longitudinal axis and intersecting both the longitudinal axis and the lower transverse axis;

a first and second end lower lateral axes, said first and second end lower lateral axes are axes which are parallel to the central lower lateral axis and intersect the lower transverse axis and which pass through respective end portions;

a contact protrusion having two pairs of opposing sidewalls, at least one of the sidewalls extends from the bottom portion by about ⅜ or more, said contact protrusion having a first sidewall that is generally parallel to the lower transverse axis and has a length of about 1.5 inches or less, said contact protrusion having a second sidewall that is generally parallel to the central lower lateral axis and has a length of about 0.5 inch or less;

wherein the distance between the exterior surfaces of the end portions measured along the lateral transverse axis is about 4.25 inches or less;

wherein the distance between the exterior surfaces of the side portions along the central lower lateral axis is about 1 inch or less;

wherein the distance between the exterior surfaces of the first end portion along the first end lateral lower axis is about 1.5 inches or less;

wherein the distance between the exterior surfaces of the second end portion along the second end lateral lower axis is about 1.5 inches or less; and wherein the battery pack is substantially symmetrical about the central lateral lower axis and asymmetrical about the lower lateral transverse axis.

2. The battery pack of claim 1, further comprising a handle extending upwardly from an upper surface of the body of the battery pack.

3. The battery pack of claim 2, wherein said handle has an elongated concave portion.

4. The battery pack of claim 1, further comprising at least one pair of guard rails positioned on the interior side portion of the battery pack, said guard rails are configured to engage with a mounting surface on the portable oxygen concentrator.

5. The battery pack of claim 4, wherein said guard rails are configured to engage with a battery bail.

6. The battery pack of claim 5, wherein said battery bail is mounted on the oxygen concentrator.

7. The battery pack of claim 5, wherein said battery bail is mounted on a mobility cart.

8. The battery pack of claim 4, wherein the distance between the guard rails is between about 1 to 1.5 inches.

9. The battery pack of claim 1, further comprising a casing and a plurality of battery cells enclosed therein, wherein at least a portion of the battery cells are arranged in a side-by-side array along a non-linear path.

10. The battery pack of claim 1, wherein the contact protrusion is configured to engage with a recess formed in the portable oxygen concentrator.

11. A battery pack for providing electrical power to a portable oxygen concentrator, comprising:

a plurality of battery cells;

an asymmetrical housing having a U-shaped cross-section, wherein said housing encloses the battery cells therein and permits said battery cells to be positioned in a side-by-side arrangement along a non-linear path inside said housing;

a handle portion extending from an upper surface of the housing; and a contact protrusion extending from a lower surface of the housing for mating with power contacts on the oxygen concentrator.

12. The battery pack of claim 11, wherein the battery cells are selected from the group consisting of lithium ion cells, lithium polymer cells, nickel cadmium cells and nickel metal hydride cells.

13. The battery pack of claim 11, wherein the footprint of the battery pack has a length that is less than about 4.25 inches and a width that is less than about 1.5 inches when the battery pack is mounted in an upright position in the oxygen concentrator.

14. The battery pack of claim 1, wherein the contact protrusion extends from a lower surface of the housing by about ⅜ inch or more.

* * * * *